United States Patent
Roeder et al.

(10) Patent No.: US 9,662,196 B2
(45) Date of Patent: May 30, 2017

(54) ENDOLUMINAL PROSTHESIS WITH STEERABLE BRANCH

(71) Applicants: Cook Medical Technologies LLC, Bloomington, IN (US); The Cleveland Clinic Foundation, Cleveland, OH (US)

(72) Inventors: Blayne A Roeder, Lafayette, IN (US); Roy K Greenberg, Bratenahl, OH (US); Jarin Kratzberg, Lafayette, IN (US); Matthew S Huser, West Lafayette, IN (US)

(73) Assignees: Cook Medical Technologies LLC, Bloomington, IN (US); The Cleveland Clinic Foundation, Cleveland, OH (US)

( * ) Notice: Subject to any disclaimer, the term of this patent is extended or adjusted under 35 U.S.C. 154(b) by 765 days.

(21) Appl. No.: 13/626,166

(22) Filed: Sep. 25, 2012

(65) Prior Publication Data

US 2013/0079870 A1  Mar. 28, 2013

Related U.S. Application Data

(60) Provisional application No. 61/539,700, filed on Sep. 27, 2011, provisional application No. 61/581,412, filed on Dec. 29, 2011.

(51) Int. Cl.
*A61F 2/07*       (2013.01)
*A61F 2/954*      (2013.01)
(Continued)

(52) U.S. Cl.
CPC  *A61F 2/07* (2013.01); *A61F 2/89* (2013.01); *A61F 2/954* (2013.01);
(Continued)

(58) Field of Classification Search
CPC ........................ A61F 2/07–2002/075
See application file for complete search history.

(56) References Cited

U.S. PATENT DOCUMENTS 6,187,033 B1   2/2001  Schmitt et al. ............ 623/1
6,645,242 B1   11/2003 Quinn ..................... 623/1.16
(Continued)

FOREIGN PATENT DOCUMENTS

AU   2010202544 B1   8/2010  ............ A61F 2/90
JP   2007-523694 A   8/2007
(Continued)

OTHER PUBLICATIONS

Extended European Search Report for EP 12275151.4, dated Jan. 21, 2013, pp. 1-8, European Patent Office, Munich, Germany.
(Continued)

*Primary Examiner* — Yashita Sharma
*Assistant Examiner* — Rebecca Preston
(74) *Attorney, Agent, or Firm* — Brinks Gilson & Lione

(57) ABSTRACT

An endoluminal prosthesis may include a tubular main graft body including a sidewall and proximal and distal ends. A first stent may be positioned near the proximal end of the main graft body. A second stent may be positioned adjacent to and distal of the first stent. An opening in the sidewall may be positioned longitudinally between a peak of the first stent and a valley of the second stent. A tubular branch may be disposed in the opening. The branch may include first and second end openings. The branch may be flexibly orientable between a retrograde configuration in which the first end opening is oriented toward the distal end and the second end opening is oriented toward the proximal end and an antegrade configuration in which the first end opening is oriented toward the proximal end and the second end opening is oriented toward the distal end.

14 Claims, 23 Drawing Sheets

(51) Int. Cl.
*A61F 2/06* (2013.01)
*A61F 2/95* (2013.01)
*A61F 2/89* (2013.01)

(52) U.S. Cl.
CPC ... *A61F 2002/061* (2013.01); *A61F 2002/075* (2013.01); *A61F 2002/9511* (2013.01); *A61F 2220/005* (2013.01); *A61F 2220/0025* (2013.01); *A61F 2220/0033* (2013.01); *A61F 2220/0066* (2013.01); *A61F 2220/0075* (2013.01); *A61F 2230/0006* (2013.01); *A61F 2250/0006* (2013.01)

(56) References Cited

U.S. PATENT DOCUMENTS

| | | | |
|---|---|---|---|
| 6,652,567 B1 | 11/2003 | Deaton | 623/1.1 |
| 6,723,116 B2 | 4/2004 | Taheri | 623/1.11 |
| 7,232,459 B2 | 6/2007 | Greenberg et al. | 623/1.13 |
| 7,537,606 B2 | 5/2009 | Hartley et al. | 623/1.11 |
| 7,611,529 B2 | 11/2009 | Greenberg et al. | 623/1.11 |
| 7,758,626 B2* | 7/2010 | Kim | A61F 2/07 606/108 |
| 7,976,575 B2 | 7/2011 | Hartley | 623/1.11 |
| 2004/0230287 A1* | 11/2004 | Hartley | A61F 2/07 623/1.12 |
| 2005/0060027 A1* | 3/2005 | Khenansho | A61F 2/82 623/1.35 |
| 2005/0131517 A1* | 6/2005 | Hartley et al. | 623/1.13 |
| 2006/0004433 A1 | 1/2006 | Greenberg et al. | 623/1.11 |
| 2006/0095118 A1 | 5/2006 | Hartley | 623/1.35 |
| 2006/0247761 A1* | 11/2006 | Greenberg | A61F 2/07 623/1.16 |
| 2007/0219621 A1 | 9/2007 | Hartley et al. | |
| 2007/0244542 A1* | 10/2007 | Greenan | A61F 2/07 623/1.13 |
| 2008/0114445 A1* | 5/2008 | Melsheimer et al. | 623/1.13 |
| 2008/0228260 A1* | 9/2008 | Hannay | A61F 2/07 623/1.13 |
| 2008/0294234 A1 | 11/2008 | Hartley et al. | 623/1.12 |
| 2009/0125096 A1* | 5/2009 | Chu | A61F 2/07 623/1.14 |
| 2009/0125100 A1 | 5/2009 | Mead | 623/1.35 |
| 2009/0204198 A1 | 8/2009 | Jensen et al. | 623/1.11 |
| 2009/0248135 A1* | 10/2009 | Bruszewski | A61F 2/07 623/1.16 |
| 2009/0254170 A1 | 10/2009 | Hartley et al. | 623/1.12 |
| 2009/0276027 A1* | 11/2009 | Glynn | A61F 2/95 623/1.11 |
| 2010/0063576 A1 | 3/2010 | Schaeffer et al. | 623/1.13 |
| 2010/0268327 A1 | 10/2010 | Bruszewski et al. | 623/1.18 |
| 2010/0312326 A1 | 12/2010 | Chuter et al. | 623/1.13 |
| 2011/0054594 A1 | 3/2011 | Mayberry et al. | 623/1.34 |
| 2011/0288627 A1* | 11/2011 | Hartley | A61F 2/07 623/1.13 |
| 2011/0313512 A1 | 12/2011 | Hartley et al. | 623/1.35 |
| 2012/0172965 A1* | 7/2012 | Kratzberg | A61F 2/962 623/1.12 |
| 2012/0271401 A1* | 10/2012 | Bruszewski et al. | 623/1.15 |

FOREIGN PATENT DOCUMENTS

| | | | |
|---|---|---|---|
| JP | 2011-512217 A | 4/2011 | |
| WO | WO 2005/067660 A2 | 7/2005 | |
| WO | WO 2006/034276 A1 | 3/2006 | A61F 2/06 |
| WO | WO 2009/104000 A1 | 8/2009 | |
| WO | WO 2010/024879 A1 | 3/2010 | A61F 2/06 |
| WO | WO 2010/063576 A1 | 6/2010 | B22F 9/08 |
| WO | WO 2010/120550 A1 | 10/2010 | |
| WO | WO 2011/100290 A1 | 8/2011 | A61F 2/06 |

OTHER PUBLICATIONS

Patent Examination Report No. 1 for corresponding Australian Patent Application No. 2012227333 dated Feb. 22, 2014 (4 pages).
Examination Report for corresponding EP Application No. 12275151.4, dated Nov. 4, 2015 (5 pages).
Office Action and English translation for JP Application No. 2012-213496 dated Aug. 2, 2016, 9 pages.

* cited by examiner

ENDOLUMINAL PROSTHESIS WITH STEERABLE BRANCH

CROSS-REFERENCE TO RELATED APPLICATIONS

This application claims priority and the benefit of provisional U.S. Patent Application Ser. No. 61/539,700, filed Sep. 27, 2011, and provisional U.S. Patent Application Ser. No. 61/581,412, filed Dec. 29, 2011, each of which is incorporated herein by reference in its entirety.

TECHNICAL FIELD

This disclosure relates to medical devices for implantation within the human or animal body for treatment of endovascular disease.

BACKGROUND

The present disclosure relates generally to medical devices. More particularly, it relates to an endoluminal prosthesis with a steerable branch.

Endovascular methods have been proposed for treatment of diseases of the aorta such as aortic dissection and aortic aneurysm. Using stent grafts to treat aneurysms is common in the medical field. Stent grafts are deployed by accessing a vasculature with a small incision in the skin and guiding a delivery system to the target area. This endoluminal delivery is less invasive and generally preferred over more intrusive forms of surgery. Multiple stent grafts may be implanted using endoluminal delivery to provide a system of interconnected stent grafts. Interconnected stent grafts can be made of fenestrated stent grafts and smaller side branch grafts, including bifurcated components.

Such methods have been proposed particularly when the diseased portion of the aorta is adjacent the aorta bifurcation. But when the diseased portion of the aorta is located higher up in the aorta, for example, in the region of the descending aorta adjacent the thoracic arch or in the ascending aorta, endovascular techniques for treating these diseases are somewhat more difficult because of the arched or curved nature of the thoracic arch, the presence of major arteries in the region, and the proximity to the heart.

Custom made devices, including scalloped and fenestrated devices, have been used in situations where the arch vessels are compromised and entire coverage of the aortic arch is not required. However, deployment of these devices may be difficult.

SUMMARY

The present embodiments provide an endoluminal prosthesis with a steerable branch.

In one example, an endoluminal prosthesis may include a tubular main graft body. The main graft body may include a sidewall, a proximal end, and a distal end. A first stent may be positioned near the proximal end of the main graft body. A second stent may be positioned adjacent to and distal of the first stent. Each of the first stent and the second stent may include a peak and a valley. The main graft body may include an opening in the sidewall positioned longitudinally between the peak of the first stent and the valley of the second stent. The prosthesis may include a tubular branch disposed in the opening and attached to the main graft body. The branch may include a first end opening and a second end opening. The branch may be flexibly orientable between a retrograde configuration and an antegrade configuration. In the retrograde configuration, the first end opening may be oriented toward the distal end of the main graft body and the second end opening may be oriented toward the proximal end of the main graft body. In the antegrade configuration, the first end opening may be oriented toward the proximal end of the main graft body and the second end opening may be oriented toward the distal end of the main graft body.

In another example, an endoluminal prosthesis may include a main tubular graft body. The main graft body may include a proximal end and a distal end. The main graft body may include a slit extending at least partially circumferentially around the main graft body. The prosthesis may include a tubular branch disposed in the slit. The branch may include a first portion extending inward from the main graft body, a second portion extending outward from the main graft body, ad an intermediate portion attached to the main graft body adjacent to the slit. The second portion of the branch may be flexibly orientable toward the proximal end or the distal end of the main graft body.

In another example, a method of treating a body vessel may include introducing an endoluminal prosthesis into the body vessel. The prosthesis may include a tubular main graft body. The main graft body may include a sidewall, a proximal end, and a distal end. The main graft body may include an opening in the sidewall of the main graft body. The prosthesis may include a tubular branch disposed in the opening and attached to the main graft body. The branch may include a first end opening and a second end opening. The first end opening may be flexibly orientable toward the proximal end or the distal end of the main graft body. The method may include introducing a balloon into the branch to move the branch into a desired orientation relative to the graft body. The method may include deploying a branch prosthesis within the branch in the desired orientation to connect the prosthesis to a branch vessel.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTIONS OF THE DRAWINGS

DETAILED DESCRIPTION OF THE DRAWINGS AND THE PRESENTLY PREFERRED EMBODIMENTS

Figure 1:
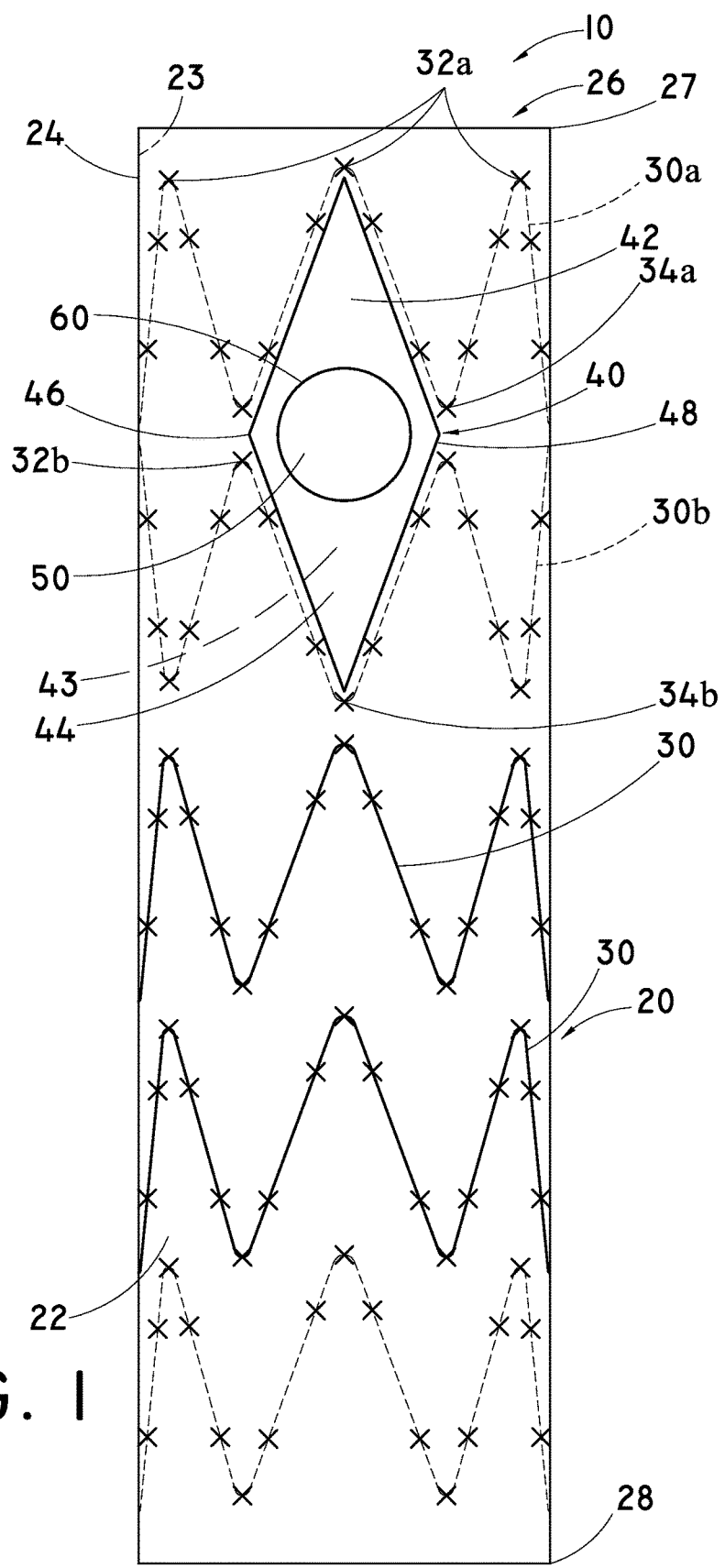
FIG. 1 is a perspective view of one embodiment of an endoluminal prosthesis.

The present disclosure relates to an endoluminal prosthesis with a steerable branch.

In the present disclosure, the term "proximal" refers to a direction that is generally closest to the heart during a medical procedure, while the term "distal" refers to a direction that is farthest from the heart during a medical procedure.

FIGS. 1-5 depict one example of a prosthesis 10. In one example, the prosthesis 10 may be configured as a single branch thoracic endograft that provides flow to the left subclavian artery or the left common carotid artery as further described below. In other examples, the prosthesis 10 may be applied to extend coverage more proximal by using the single branch for the left common carotid artery and relying on flow through the vertebrals or an extra-atomic bypass to maintain flow to the left subclavian artery. The prosthesis 10 may be applicable to treat aneurysms and/or dissections that require more proximal coverage than a standard thoracic stent graft might allow. The prosthesis 10 may include a graft body 20. The graft body 20 may include a graft material 22 having an inner surface 23 and an outer surface 24. The graft body 20 may be configured as a generally tubular member having a substantially cylindrical shape. The inner surface 23 of the graft material 22 may define a main lumen 26 extending longitudinally within the graft body 20 between a proximal end 27 and a distal end 28 thereof. The main lumen 26 may be suitable for passing a fluid such as, for example, blood therethrough.

The graft material 22 may be made of any material known in the art. Preferably, the graft material 22 may be formed from a biocompatible material that is substantially non-toxic in the in vivo environment of its intended use and substantially unrejected by the patient's physiological system (i.e., is non-antigenic). For example, the graft material 22 may be made of an expanded polytetrafluoroethylene (ePTFE), polytetrafluoroethylene (PTFE), silicone, polyurethane, polyamide (nylon), polyethylene, polypropylene, polyaramids, polyacrylonitrile, cellulose, or another flexible biocompatible material. The graft material 22 also may be made of known fabric graft materials, e.g., woven polyester such as DACRON® from Invista (Wichita, Kans.), polyetherurethanes such as THORALON® from Thoratec Corporation (Pleasanton, Calif.), or polyethylene such as an ultra-high molecular weight polyethylene (UHMwPE) such as DYNEEMA® from DSM Dyneema LLC (Stanley, N.C.). Additionally, or alternatively, materials that are not inherently biocompatible may be subjected to surface modifications to render the materials biocompatible. Examples of surface modifications may include, for example, graft polymerization of biocompatible polymers on the surface, coating of the surface with a crosslinked biocompatible polymer, chemical modification with biocompatible functional groups, or immobilization of a compatibilizing agent such as heparin or other biocompatible substances. Thus, any fibrous material having sufficient strength to survive in the in vivo environment may be used to form a textile graft, provided the final textile is biocompatible.

The graft material 22 may include a bioremodelable material such as reconstituted or naturally-derived collagenous materials, extracellular matrix (ECM) material, submucosa, renal capsule membrane, dermal collagen, dura mater, pericardium, fascia lata, serosa, peritoneum or basement membrane layers, or intestinal submucosa, including small intestinal submucosa (SIS), stomach submucosa, urinary bladder submucosa, or uterine submucosa. One non-limiting example of a suitable remodelable material is SURGISIS® BIODESIGN™ from Cook Medical (Bloomington, Ind.). Another suitable remodelable material is the graft prosthesis material described in U.S. Pat. No. 6,206,931 to Cook et al., which is incorporated herein by reference in its entirety. Additionally, or alternatively, the graft material 22 may be made of any of the materials described in U.S. Pat. No. 7,407,509 to Greenberg et al. or U.S. Patent Application Pub. No. 2009/0171451 by Kuppurathanam et al., which are incorporated herein by reference in their entirety.

The graft body 20 may include at least one support structure 30, such as a stent. The support structure 30 may be configured as a single, unitary structure or a plurality of independent structures. The support structure 30 and/or various portions thereof may be disposed on the inner surface 23 and/or the outer surface 24 of the graft material 22. Multiple support structures 30 may be positioned at one or more points along a length of the graft body 20. One or more support structures 30 may be positioned proximate the proximal end 27 and/or the distal end 28 of the graft body 20 to seal the respective ends of the graft body against a wall of a body vessel. The support structures 30 positioned proximate the proximal end 27 and/or the distal end 28 of the graft body 20 may be positioned on the inner surface and/or the outer surface of the graft body 20. In some instances, it may be desirable to affix one or more of the stents to an internal surface of a prosthesis. For example, in complex anatomical situations, stents affixed to an external surface of a prosthesis may have the potential to become intertwined with the wires or other devices utilized to ensure branch vessel access, sealing, or fixation.

The support structures 30 and/or various portions thereof may be stents having any suitable stent pattern known in the art. The stents may be balloon expandable. Preferably, the stents may be self-expandable. The stents can maintain the patency of the prosthesis and ensure adequate sealing against the surrounding vascular tissue. Some of the goals for stent design and placement, whether internal or external, may include preventing metal-to-metal contact points, preventing contact between two different types of alloys, and minimizing micromotion. Preferably, stent sizing, spacing, and design may be determined so that there is no stent-to-stent contact even in tortuous anatomy. Stents preferably may be placed to maximize prosthesis flexibility while maintaining patency, as well as reducing material wear and stent fatigue. Furthermore, it may be preferable that the stents do not interfere with any branches of the prosthesis, as further described below, that they minimize the potential for galvanic corrosion, and that they ensure adequate joint stability. Stent amplitude, spacing, and stagger preferably may be optimized for each prosthesis design. Any of the stents mentioned herein may have barbs and/or other anchoring members to help decrease the potential for prosthesis migration. Barbs may limit migration of the prosthesis 10. Additionally, or alternatively, barbs may reduce the potential for crushing or dislodging the branch 60 which may be caused by migration of the prosthesis 10 relative to a branch vessel. In some situations, such as treatment of an aortic dissection, it may be desirable for the prosthesis 10 to be particularly atraumatic. To that end, barbs may be omitted from the prosthesis 10 in some embodiments.

One example of a stent pattern is the Z-stent or Gianturco stent design. Each Z-stent may include a series of substantially straight segments, or struts, interconnected by a series of bent segments, or bends. The bent segments may include acute bends or apices. The Z-stents may be arranged in a zigzag configuration in which the straight segments are set at angles relative to one another and are connected by the bent segments. This design provides both significant radial force as well as longitudinal support. In tortuous anatomy, branches, or fenestrations, it may be preferable to use alternative stents or modifications to the Z-stent design to avoid stent-to-stent contact. Alternative stents may include, for example, annular or helical stents.

The stents described herein may be made from any suitable material known in the art. In one example, the stents may be made from standard medical grade stainless steel and may be soldered using silver standard solder (0 lead/0 tin). In other examples, the stents may be made from a metallic material selected from any type of stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($La_2O_3$), and a nickel-titanium alloy, or other suitable materials known in the art. The stents may be made from nitinol or other shape-memory metal. Moreover, the stents may be configured in a variety of ways to provide a suitable intraluminal support structure. For example, one or more stents may be made from a woven wire structure, a laser-cut cannula, individual interconnected rings, or another pattern or design.

A deformable region 40 may be disposed on the graft material 22 of the graft body 20. The deformable region 40 may include a biocompatible graft material 42. The graft material 42 may be formed from any material known in the art. For example, the graft material 42 may be formed from any of the materials described above with reference to the graft material 22. The graft material 42 may be formed from the same or a different material than the material used to form the graft material 22. The deformable region 40 may be formed integrally with the graft body 20. To that end, the graft material 22 and the graft material 42 may be formed from a unitary piece of graft material. The deformable region 40 may be formed during a weaving process used to produce the unitary piece of graft material. For example, a number of warp yarns and/or a number of weft yarns may be adjusted during the weaving process to form excess graft material as described in U.S. Patent Application Pub. No. 2010/0063576 by Schaeffer et al., which is incorporated by reference herein in its entirety.

Additionally, or alternatively, the deformable region 40 may be attached to the graft body 20. The deformable region 40 may be attached to the graft body 20 by sutures, wire, staples, clips, bonding agents, or other methods that may be used to achieve a secure attachment. For example, the deformable region 40 may be attached to the graft body 20 by any method described in U.S. Patent Application Pub. No. 2006/0095118 by Hartley, which is incorporated by reference herein in its entirety. The deformable region 40 may be attached to the graft material 22 and/or the support structure 30 of the graft body 20. Preferably, the graft material 42 of the deformable region 40 may be attached to the graft material 22 of the graft body 20 to form a fluid-tight seal. For example, the graft material 42 of the deformable region 40 may be stitched to the graft material 22 of the graft body 20. An opening may be formed through the graft material 22 of the graft body 20 and may correspond to the deformable region 40. The deformable region 40 may be positioned within the opening such that an inner surface 43 of the deformable region is generally contiguous with the inner surface 23 of the graft body 20 and an outer surface 44 of the deformable region is generally contiguous with the outer surface 24 of the graft body. In other words, the deformable region 40 may be positioned within the opening such that the inner surface 43 is in communication with the lumen 26 of the graft body 20.

An outer edge of the deformable region 40 may be defined by a perimeter 46. The perimeter 46 may be positioned within a space defined by one or more of the support structures 30 of the graft body 20. For example, a first proximal stent 30a may be positioned proximate the proximal end 27 of the graft body 20 as shown in FIG. 1. The first proximal stent 30a may be disposed on the inner surface 23 of the graft material 22. A second proximal stent 30b may be positioned proximate and distal to the first proximal stent 30a. The second proximal stent 30b may be disposed on the inner surface 23. The first proximal stent 30a may have a series of peaks 32a formed by proximal bends and a series of valleys 34a formed by distal bends. Similarly, the second proximal stent 30b may have a series of peaks 32b formed by proximal bends and a series of valleys 34b formed by distal bends. The first and second proximal stents 30a, 30b may be positioned relative to one another such that a peak 32a of the first proximal stent is aligned with a valley 34b of the second proximal stent along a circumference of the graft body 20. The first proximal stent 30a and the second proximal stent 30b may be arranged on the graft body 20 to be mirror images of one another with respect to a circumference of the graft body as shown in FIG. 1.

The first proximal stent 30a may be positioned near the proximal end 27 of the graft body 20. In one example, a peak 32a of the first proximal stent 30a may be spaced from the proximal end 27 of the graft body 20 by a distance of less than about 2 mm, typically between about 0.5 mm and about 1 mm. The proximity of the first proximal stent 30a to the proximal end 27 of the graft body 20 may reduce the amount of unsupported graft material at the proximal end of the graft body. This may reduce the probability of graft infolding and/or movement of the graft material (e.g., in response to blood flow), which may cause graft fatigue. In other examples, the first proximal stent 30a may be spaced any suitable distance from the proximal end of the graft body.

Additionally, or alternatively, the first proximal stent 30a and the second proximal stent 30b may be spaced longitudinally from one another by a distance (e.g., between a valley 34a and a peak 32b) of between about 2 mm and about 20 mm, typically between about 5 mm and about 13 mm. In one example, the spacing between the first proximal stent 30a and the second proximal stent 30b may vary circumferentially around the graft body 20. For example, a top longitudinal length of the prosthesis may be greater than a bottom longitudinal length of the prosthesis (e.g., to form a slanted end as further described below). The spacing between the first proximal stent 30a and the second proximal stent 30b along the top longitudinal length may be greater than the spacing between the first proximal stent and the second proximal stent along the bottom longitudinal length. In one example, the first proximal stent 30a and the second proximal stent 30b may be spaced longitudinally from one another by a distance of between about 5 mm and about 15 mm, typically between about 7 mm and about 13 mm, preferably about 10 mm along the top longitudinal length. Additionally, or alternatively, the first proximal stent 30a and the second proximal stent 30b may be spaced longitudinally from one another by a distance of between about 2 mm and about 7 mm, typically about 5 mm along the bottom longitudinal length. The spacing between other portions of the support structure 30 (e.g., between other adjacent stents) may be similar to the spacing between the first proximal stent 30a and the second proximal stent 30b. In other examples, adjacent stents may be spaced any suitable distance from one another.

The perimeter 46 of the deformable region 40 may correspond to a space generally bounded on its proximal sides by one peak 32a and the two adjacent struts of the first proximal stent 30a and on its distal sides by one valley 34b, which may be in alignment with the one peak 32a, and the two adjacent struts of the second proximal stent 30b. In this manner, the graft material 42 of the deformable region 40 positioned within the perimeter 46 may be unstented. In other words, the support structure 30 of the graft body 20 may be positioned substantially outside of the deformable region 40. The lack of support structure within the perimeter 46 of the deformable region 40 may enable the graft material 42 to deform as further described below.

The perimeter 46 may include a frame 48. The frame 48 may add structural support to the deformable region 40 and/or the attachment between the graft material 42 of the deformable region and the graft material 22 of the graft body 20. The frame 48 may be configured as a rigid, semi-rigid, or flexible frame. Preferably, the frame 48 may be a flexible frame formed from any material known in the art including, for example, the materials described above with reference to the support structure 30. The perimeter 46 may have any desired geometric shape. For example, the perimeter 46 may have a diamond shape as shown in FIGS. 1-5. The diamond shape may be generally defined by the struts and bends of the first and second proximal stents 30a, 30b as described above. The diamond shape may include a long axis extending substantially parallel to the longitudinal axis of the graft body 20 and a short axis extending substantially perpendicular to the longitudinal axis of the graft body. Alternatively, the perimeter 46 may have a circular, triangular, rectangular, or any other polygonal or non-polygonal geometric shape. Preferably, the perimeter 46 may be disposed substantially between the support structure 30 of the graft body 20 regardless of the shape of the perimeter. This may provide a substantially unstented deformable region 40 to enable deformation of the graft material 42 within the perimeter 46.

As best shown in FIGS. 2-5, the graft material 42 of the deformable region 40 may be deformable within the perimeter 46. For example, the graft material 42 may be bunched, folded, pleated, gathered, stretched, or otherwise manipulated within the perimeter 46. To that end, the graft material 42 may be configured as an elastic material. Suitable elastic materials may include polymers such as polyeurethanes. Additionally, or alternatively, the graft material 42 may be woven in a suitable manner to provide elastic properties to the graft material. Alternatively, or additionally, the deformable region 40 may include excess graft material 42 to enable deformation. For example, a piece of graft material 42 used to form the deformable region 40 may have a larger surface area than the area within the perimeter 46. Thus, excess graft material 42 may be disposed within the perimeter 46 of the deformable region 40 when the piece of graft material 42 is attached to or formed with the graft material 22 of the graft body 20 as described above. This excess graft material may enable movement of the graft material 42 of the deformable region 40 relative to the graft body 20.

The prosthesis 10 may include a branch 60. The branch 60 may include a graft material 62 having an inner surface 63 and an outer surface 64. The branch 60 may be configured as a generally tubular member having a substantially cylindrical shape. The inner surface 63 of the graft material 62 may define a branch lumen 66 extending longitudinally within the branch 60 between a first end 67 and a second end 68 thereof.

The graft material 62 may be formed from any material known in the art. For example, the graft material 62 may be formed from any of the materials described above with reference to the graft material 22 and/or the graft material 42. The graft material 62 may be formed from the same or a different material than the material used to form the graft material 22 and/or the graft material 42. The branch 60 may be formed integrally with the graft body 20 and/or the deformable region 40. To that end, the graft material 22, the graft material 42, and/or the graft material 62 may be formed from a unitary piece of graft material. Alternatively, the branch 60 may be attached to the deformable region 40 and/or the graft body 20. The branch 60 may be attached to the deformable region 40 and/or the graft body 20 by sutures, wire, staples, clips, bonding agents, or other methods that may be used to achieve a secure attachment including, for example, the methods described above with reference to the deformable region 40. In another example, the branch 60 may be unattached to the deformable region 40.

The branch 60 may include at least one support structure 70. The support structure 70 may include a single, unitary structure or a plurality of independent structures. The support structure 70 and/or various portions thereof may be disposed on the inner surface 63 and/or the outer surface 64 of the branch 60. Multiple support structures 70 may be positioned at any points along a length of the branch 60. In one example, the support structure 70 may be configured as a helical stent extending generally longitudinally and circumferentially along the branch 60. The support structure 70 also may be configured as one or more annular rings positioned along the length of the branch 60. Alternatively, or additionally, any other type of stent including, for example, those described above in reference to the support structure 30 may be used. The support structure 70 may be formed from any material known in the art including, for example, the materials described above with reference to the support structure 30.

Figure 6:
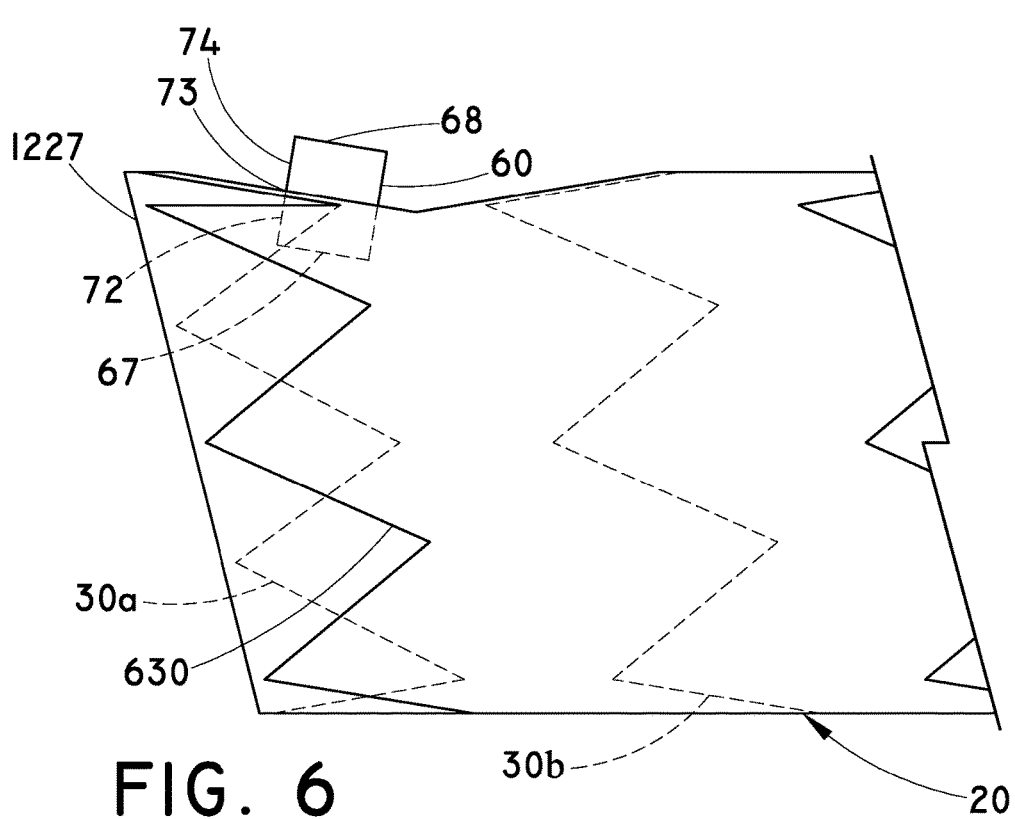
Figure 8:
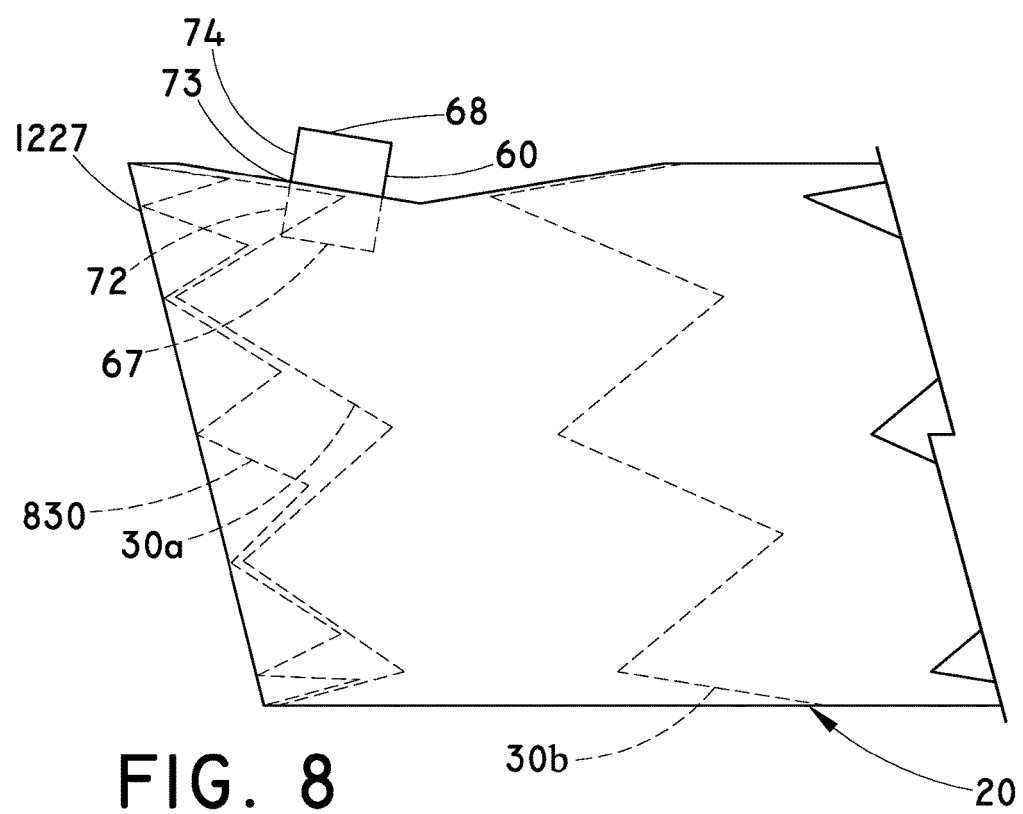
Figure 10:
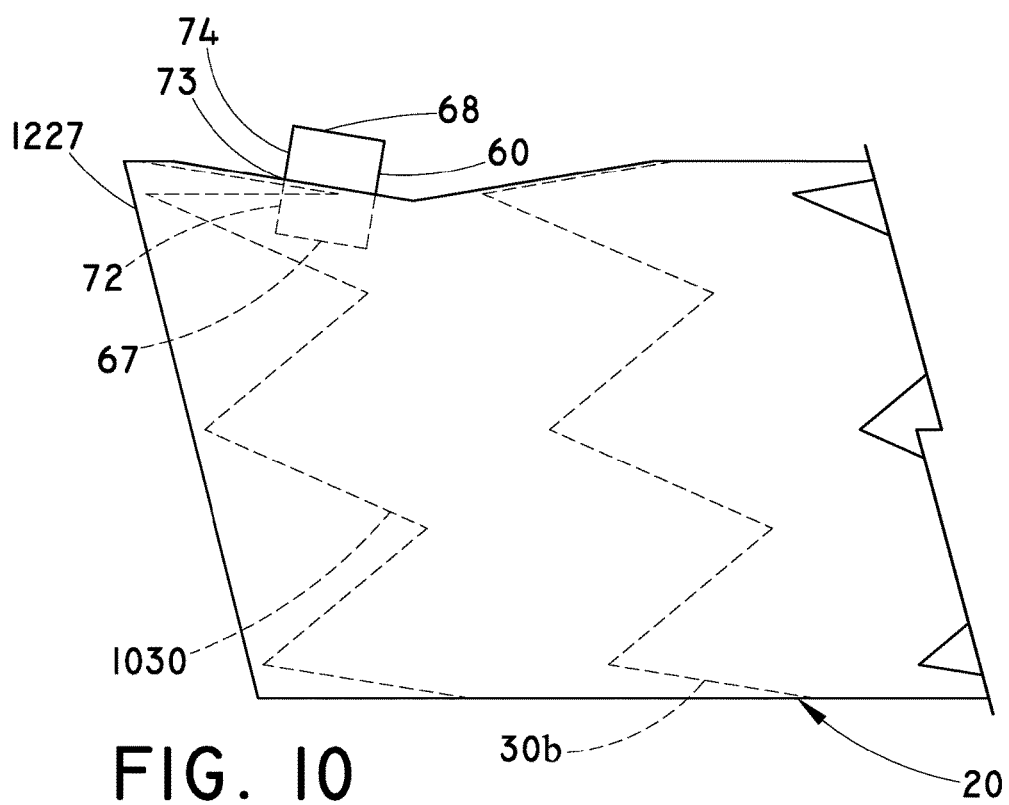

The branch 60 may extend through an aperture 50 formed in the deformable region 40. The branch 60 may extend between a position within the lumen 26 of the graft body 20 and a position external to the graft body. For example, the branch 60 may include a first portion 72 and a second portion 74 as best shown in FIGS. 6, 8, and 10. The first portion 72 of the branch 60 may extend longitudinally from the first end 67 to an intermediate point 73 positioned longitudinally between the first end and the second end 68 of the branch. The second portion 74 of the branch 60 may extend longitudinally between the intermediate point 73 and the second end 68 of the branch. The first portion 72 of the branch 60 may be positioned within the lumen 26 of the graft body 20. The second portion 74 of the branch 60 may be positioned external of the graft body 20. The intermediate point 73 may be generally aligned with the graft material 42 of the deformable region 40. The branch 60 may be attached to the deformable region 40 at about the intermediate point 73. A length of the first portion 72 of the branch 60 may range from 0 to 100% of the total length of the branch. A length of the second portion 74 of the branch 60 may range from 0 to 100% of the total length of the branch. In other words, the branch 60 may be positioned entirely within the lumen 26, entirely external to the graft body 20, or partially within the lumen 26 and partially external to the graft body. In one embodiment, the length of the first portion 72 is about 50% of the total length of the branch 60, and the length of the second portion 74 is about 50% of the total length of the branch. In other words, about half of the length of the branch 60 may be positioned within the lumen 26 of the graft body 20, and about half of the length of the branch may be positioned external to the graft body. In another embodiment, the length of the first portion 72 is about 30% of the total length of the branch 60, and the length of the second portion 74 is about 70% of the total length of the branch. In other words, about 30% of the length of the branch 60 may be positioned within the lumen 26 of the graft body 20, and about 70% of the length of the branch may be positioned external to the graft body.

Positioning a portion of the branch 60 within the lumen 26 of the graft body 20 and a portion of the branch external to the graft body may provide multiple advantages. For example, such positioning of the branch 60 may aid in moving or toggling the branch 60 into various different configurations relative to the graft body 20 as further described below. Additionally, or alternatively, such positioning of the branch 60 may aid in placement of a branch prosthesis within the branch lumen 66 to connect the branch 60 to a target branch vessel. Positioning a larger portion of the branch 60 within the lumen 26 of the graft body 20 may ease movement of the branch relative to the graft body. Positioning a larger portion of the branch 60 external to the graft body 20 may improve blood flow within the lumen 26 and/or reduce branch fatigue that may be caused by blood flowing past the portion of the branch within the lumen of the graft body. Thus the relative lengths of the first portion 72 of the branch 60 and the second portion 74 of the branch may be selected to optimize the flexibility of the branch while maintaining fluid flow within the lumen 26 of the graft body 20 and minimizing branch fatigue.

The branch 60 may be disposed at any suitable position within the deformable region. In one example, the branch 60 may be substantially centered within the deformable region. For example, the branch 60 may be positioned approximately at the intersection of the major axis and the minor axis of the diamond-shaped deformable region. Positioning the branch 60 approximately at the center of the deformable region may aid in providing a greater range of motion of the branch relative to the graft body as further described below. In other examples, the branch 60 may be positioned at any longitudinal and/or circumferential position between adjacent support structures (e.g., the first proximal stent 30a and the second proximal stent 30b). In one example, the branch may be positioned longitudinally between a peak and a valley of a support structure (e.g., the first proximal stent 30a or the second proximal stent 30b). In this manner, the branch may be positioned closer to or farther from the proximal end of the graft body.

Figure 2:
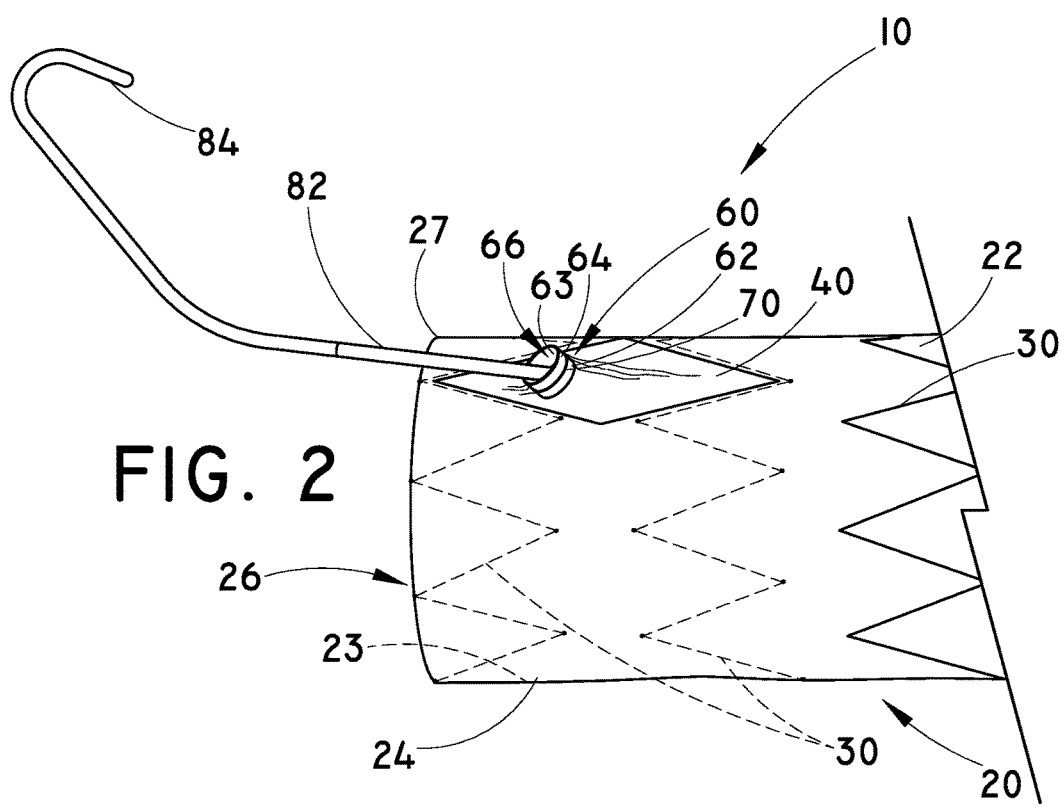
FIG. 2 is a perspective view of one embodiment of an endoluminal prosthesis with a branch in a retrograde configuration and a preloaded catheter.
Figure 3:
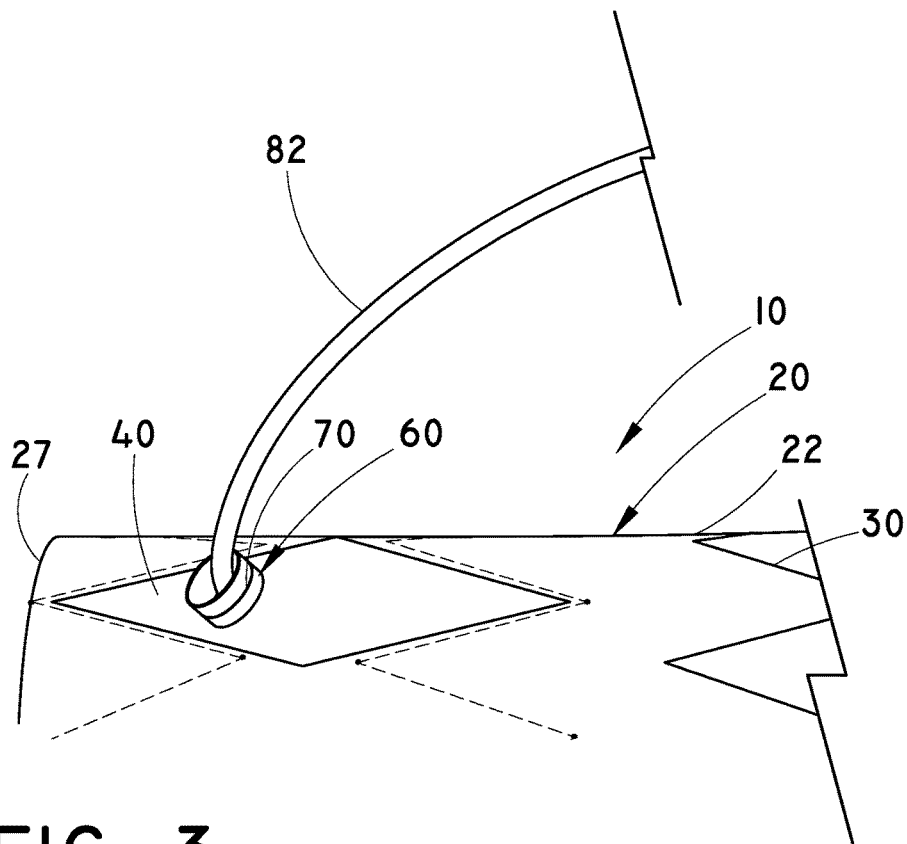
FIG. 3 is a perspective view of the endoluminal prosthesis of FIG. 2 with the catheter further advanced within the branch.
Figure 4:
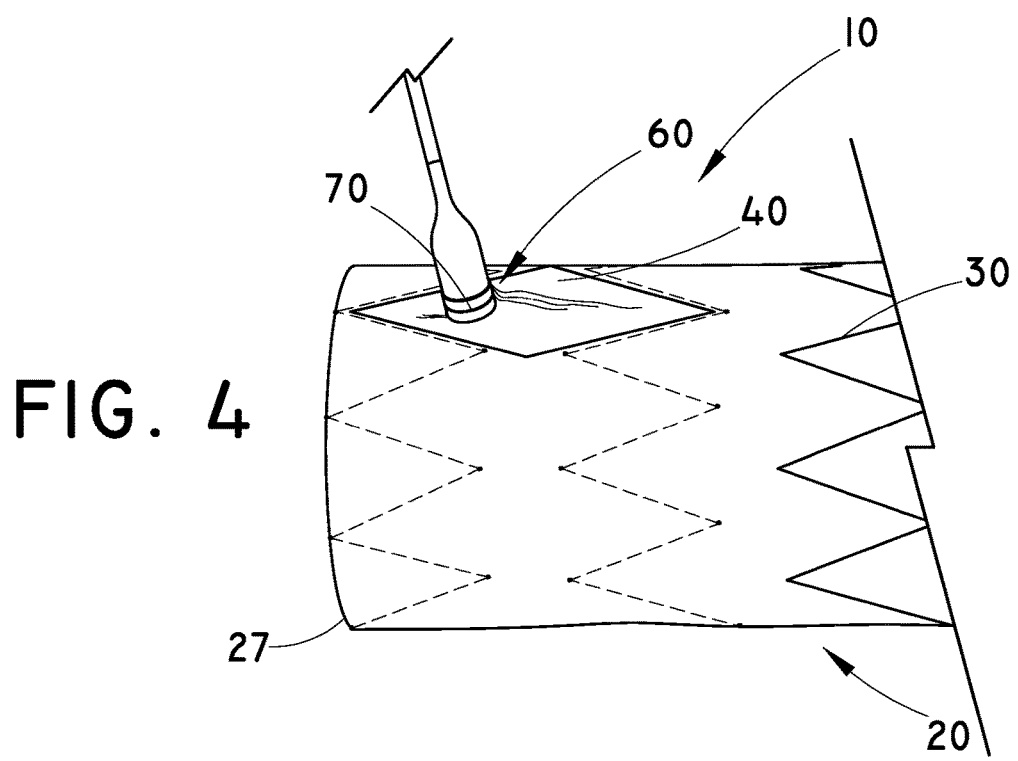
FIG. 4 is a perspective view of the endoluminal prosthesis of FIGS. 2-3 with a balloon deployed in the branch to adjust an orientation of the branch.
Figure 5:
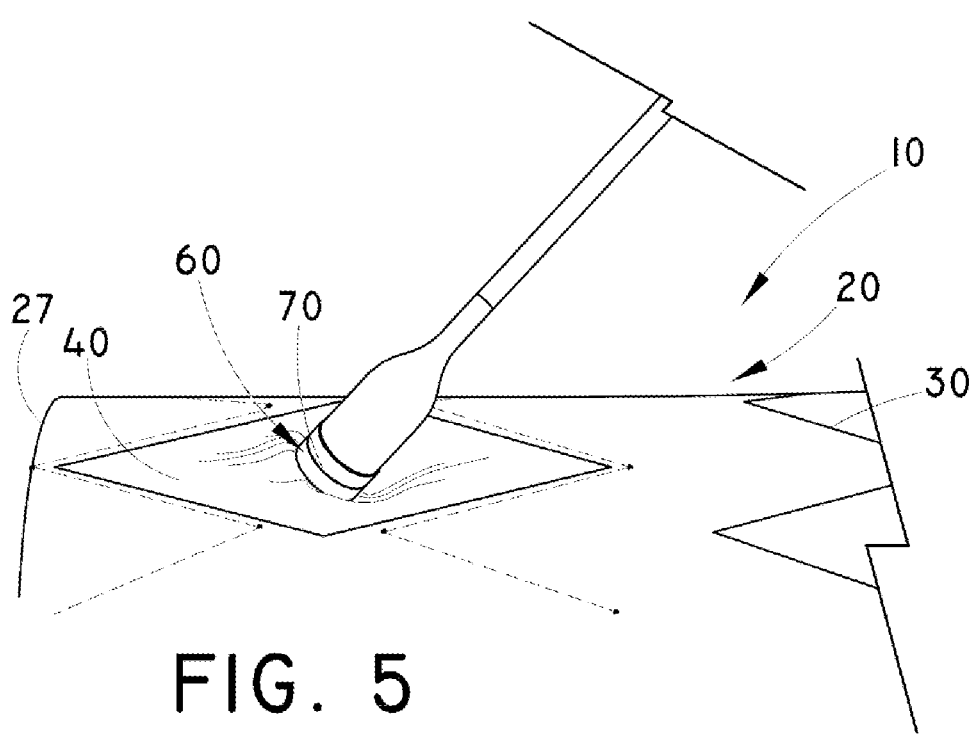
FIG. 5 is a perspective view of the endoluminal prosthesis of FIGS. 2-4 with the balloon deployed in the branch and the branch in an antegrade configuration.

The branch 60 may be movable with respect to the graft body 20. For example, the branch 60 may be attached to the deformable region 40. The graft material 42 of the deformable region 40 may be deformed to change the orientation of the branch 60 relative to the graft body 20. In one example, the branch 60 may be movable between a retrograde configuration and an antegrade configuration. FIGS. 2-4 depict the prosthesis 10 with the branch 60 in the retrograde configuration. In the retrograde configuration, the branch 60 may extend at an angle relative to the longitudinal axis of the graft body 20 with the opening of the second end 68 directed proximally and away from the outer surface 24 of the graft body external to the graft body. Accordingly, the opening of the first end 67 of the branch 60 may be directed distally and away from the inner surface 23 of the graft body 20 within the lumen 26. The angle between the outer surface 24 and the branch 60 in the retrograde configuration may range from about 0 to about 180 degrees. FIG. 5 depicts the prosthesis 10 with the branch 60 in the antegrade configuration. In the antegrade configuration, the branch 60 may extend at an angle relative to the longitudinal axis of the graft body 20 with the opening of the second end 68 directed distally and away from the outer surface 24 of the graft body external to the graft body. Accordingly, the opening of the first end 67 of the branch 60 may be directed proximally and away from the inner surface 23 of the graft body 20 within the lumen 26. The angle between the outer surface 24 and the branch 60 in the antegrade configuration may range from about 0 to about 180 degrees.

The branch 60 may be placed into the retrograde configuration, the antegrade configuration, or any other position between the retrograde configuration and the antegrade configuration. In other words, the branch 60 may be positioned at any angle with respect to the outer surface 24 of the graft body 20. The graft material 42 of the deformable region 40 may be moved relative to the graft material 22 of the graft body 20 as described above to enable movement of the branch 60 relative to the graft body. The shape of the perimeter 46 of the deformable region may be selected to bias or guide the branch 60 along a desired path of movement. For example, the diamond shaped perimeter 48 may bias the branch 60 toward a position along a long axis of the perimeter (i.e., an axis between proximal and distal points of the diamond). In other words, the opening of the second end 68 of the branch may be biased toward a plane passing through the long axis of the perimeter 48 and the longitudinal axis of the graft body 20. In this manner, the branch 60 may be configured to toggle along the plane between the retrograde and antegrade configurations. Lengthening the long axis of the diamond shaped perimeter may increase the range of motion of the branch 60 relative to the graft body 20 in the longitudinal direction (e.g., along the long axis of the perimeter). Conversely, shortening the long axis of the diamond shaped perimeter may shorten the range of motion of the branch 60 relative to the graft body 20 in the longitudinal direction. Likewise, lengthening the short axis (i.e., the axis generally transverse to the long axis) of the diamond shaped perimeter may increase the range of motion of the branch 60 relative to the graft body 20 in the circumferential direction (e.g., along the short axis of the perimeter). Conversely, shortening the short axis of the diamond shaped perimeter may shorten the range of motion of the branch 60 relative to the graft body 20 in the circumferential direction. The perimeter may be configured such that the branch 60 has a greater range of motion in the longitudinal direction than in the circumferential direction.

Although the branch 60 may be biased toward a particular direction, the branch may be movable in any direction relative to the graft body 20. For example, the branch 60 may pivot in any direction about the intermediate point 73, which may be attached to the graft material 42 of the deformable region 40, relative to the graft body 20. The openings of the first and/or second ends 67, 68 of the branch 60 may be directed in any direction (e.g., proximal, distal, or transverse) relative to the longitudinal axis of the graft body 20.

In another example, the flexibility of the deformable region 40 may enable the branch 60 to be placed in a desired orientation relative to the graft body 20 of the prosthesis 10, and the branch may remain oriented as desired after adjustment. In other words, the branch 60 may not be pulled or biased toward any orientation relative to the graft body 20.

In another embodiment, the deformable region 40 may be omitted from the prosthesis 10, and the branch 60 may be attached to the graft body 20 as shown in FIGS. 23-28. The branch 60 may be attached to a region of the graft body 20 defined between two adjacent stents (e.g., the first and second proximal stents). The region may be an unstented area between the adjacent stents. The graft material of the region of the graft body may be held in tension between the adjacent stents. For example, the region between the adjacent stents may not include excess graft material as described above with reference to the deformable region 40. The branch 60 may extend through a slit 29 formed in the graft body 20. For example, a cut may be made in the graft material of the graft body 20 to form the slit 29, and the branch 60 may be placed through the slit.

Figure 23:
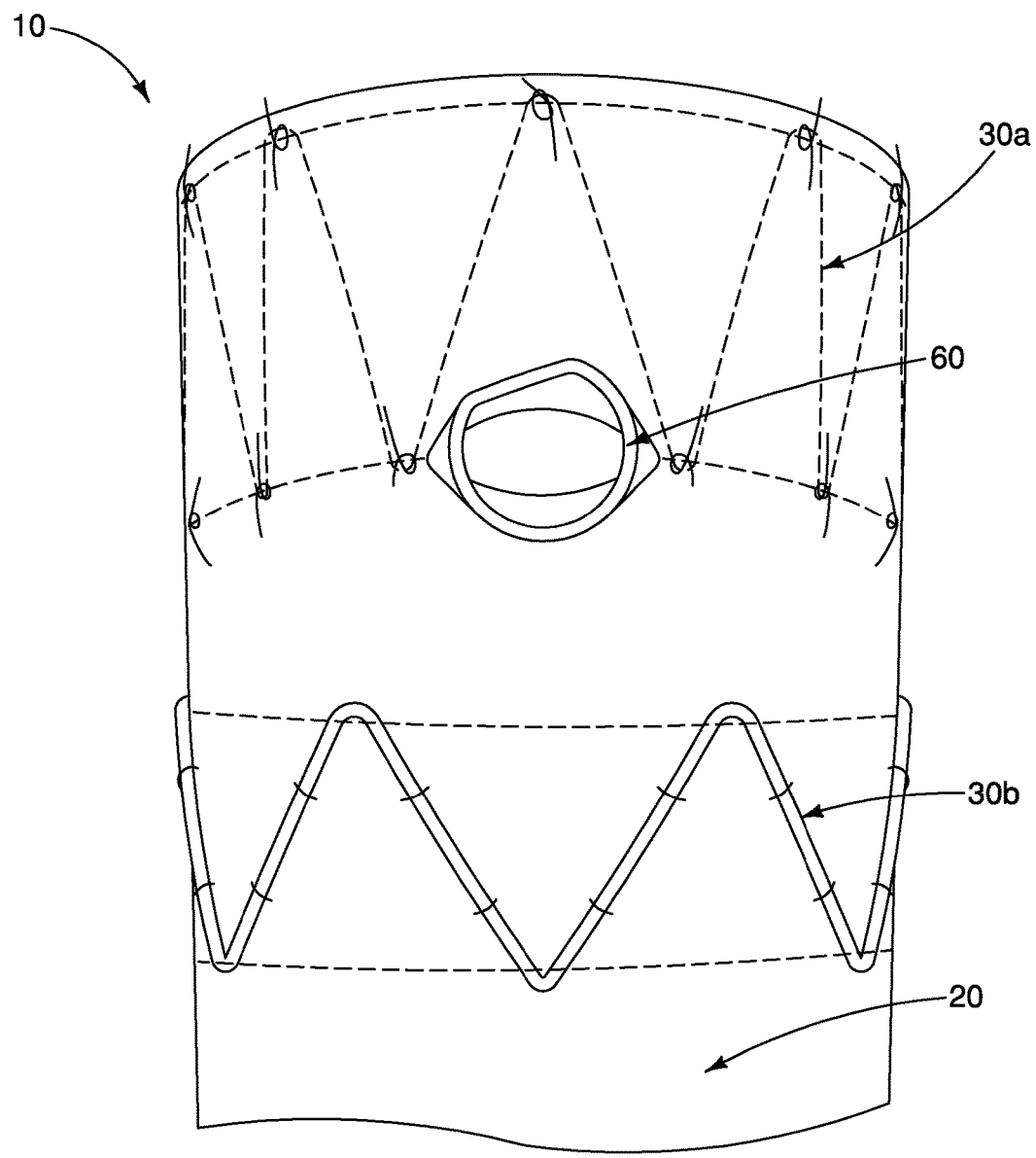
FIGS. 23-24 depict one embodiment of an endoluminal prosthesis having a branch.

In one example, the slit 29 may extend between adjacent struts of a stent (e.g., the first proximal stent) as shown in FIG. 23. This may aid in positioning the branch near the proximal end of the graft body 20 as further described below. Additionally, or alternatively, placement of the slit between adjacent struts (e.g., longitudinally at least partially between a peak and a valley of the stent) may aid in supporting the branch positioned within the slit. For example, the graft material disposed longitudinally between a peak and a valley may be held under greater tension than the graft material that is not disposed longitudinally between a peak and a valley (e.g., graft material that is disposed longitudinally distal of the valleys of the first proximal stent 30a and proximal of the peaks of the second proximal stent 30b). Placement of the branch 60 in a portion of the graft material under greater tension may aid in supporting the branch and/or biasing the branch toward a neutral configuration (e.g., between the antegrade and retrograde configurations) as shown in FIG. 23. Placement of the branch in a portion of the graft material under lesser tension may enable a greater range of motion of the branch relative to the graft body (e.g., by enabling greater movement of the graft material adjacent to the slit) and/or reduce the biasing force exerted on the branch.

Figure 24:
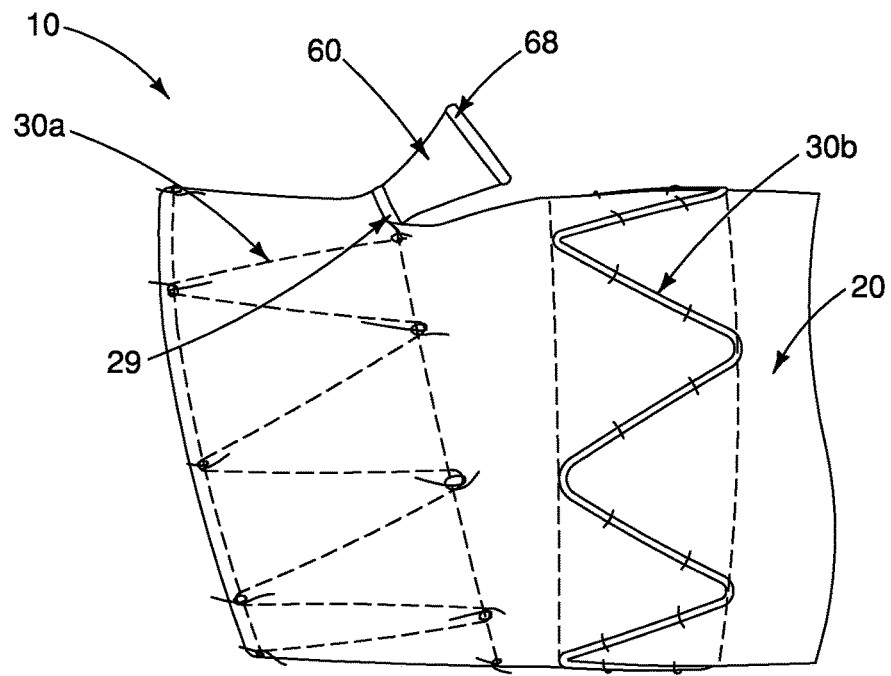
Figure 25:
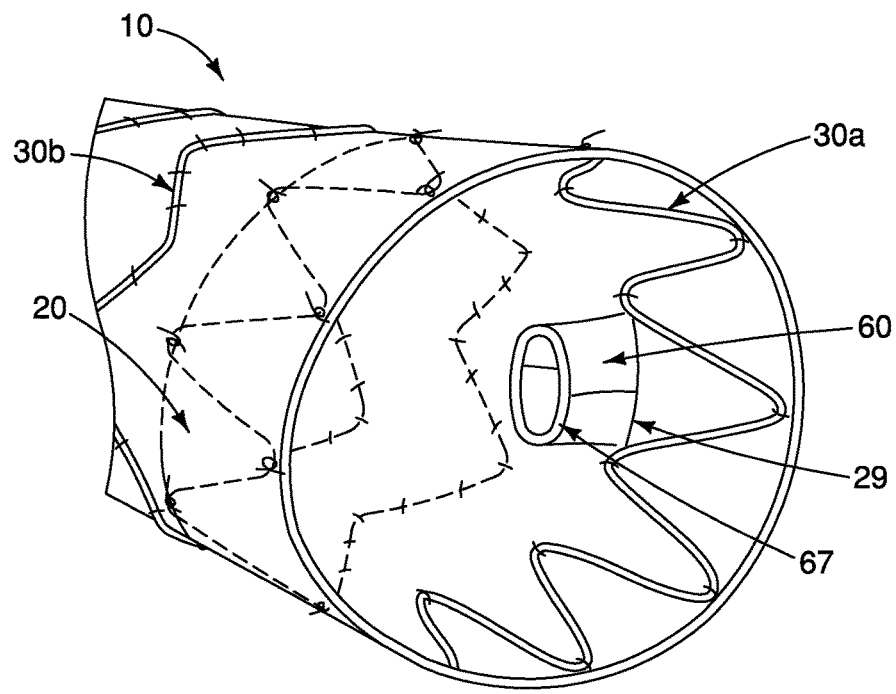
FIG. 25 depicts a lumen of the endoluminal prosthesis of FIGS. 23-24 from a proximal end of the prosthesis.
Figure 26:
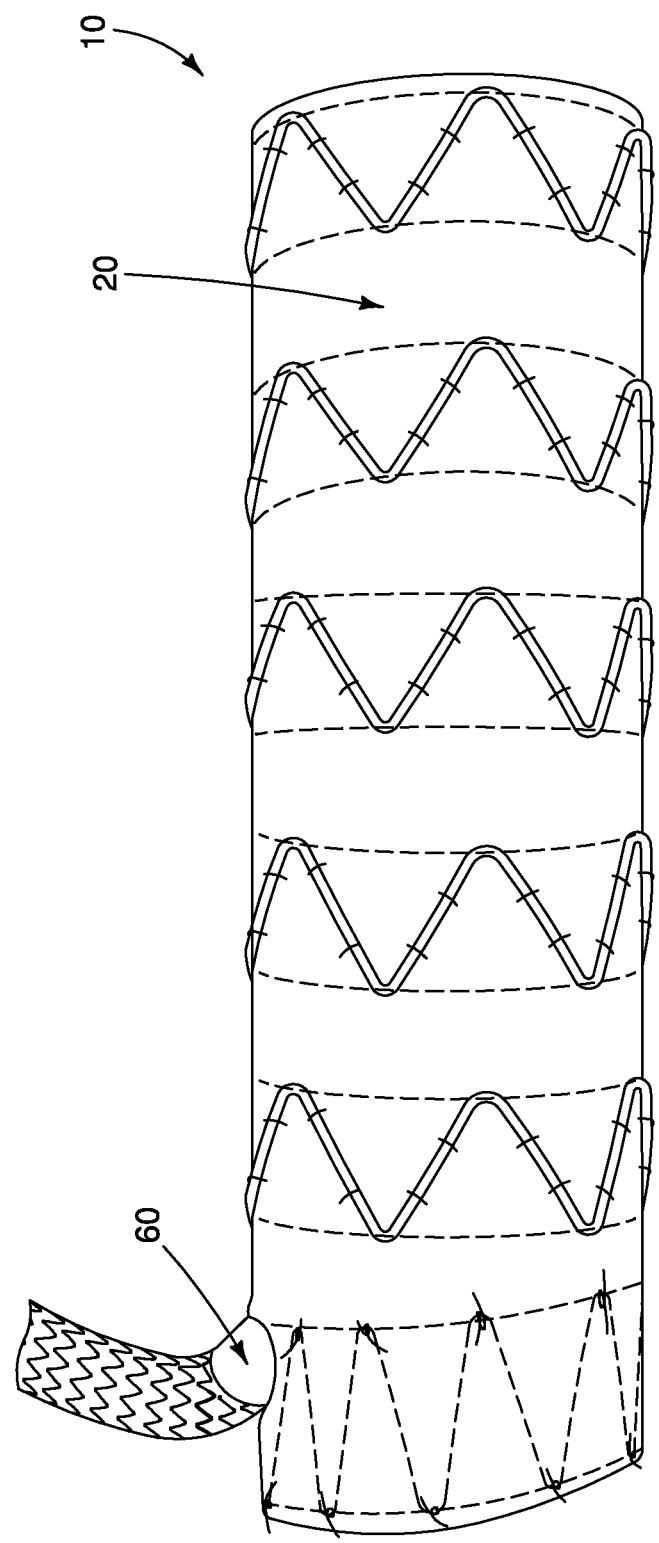
FIG. 26 depicts the endoluminal prosthesis of FIGS. 23-24 with the branch in a retrograde configuration and a branch prosthesis deployed therein.
Figure 27:
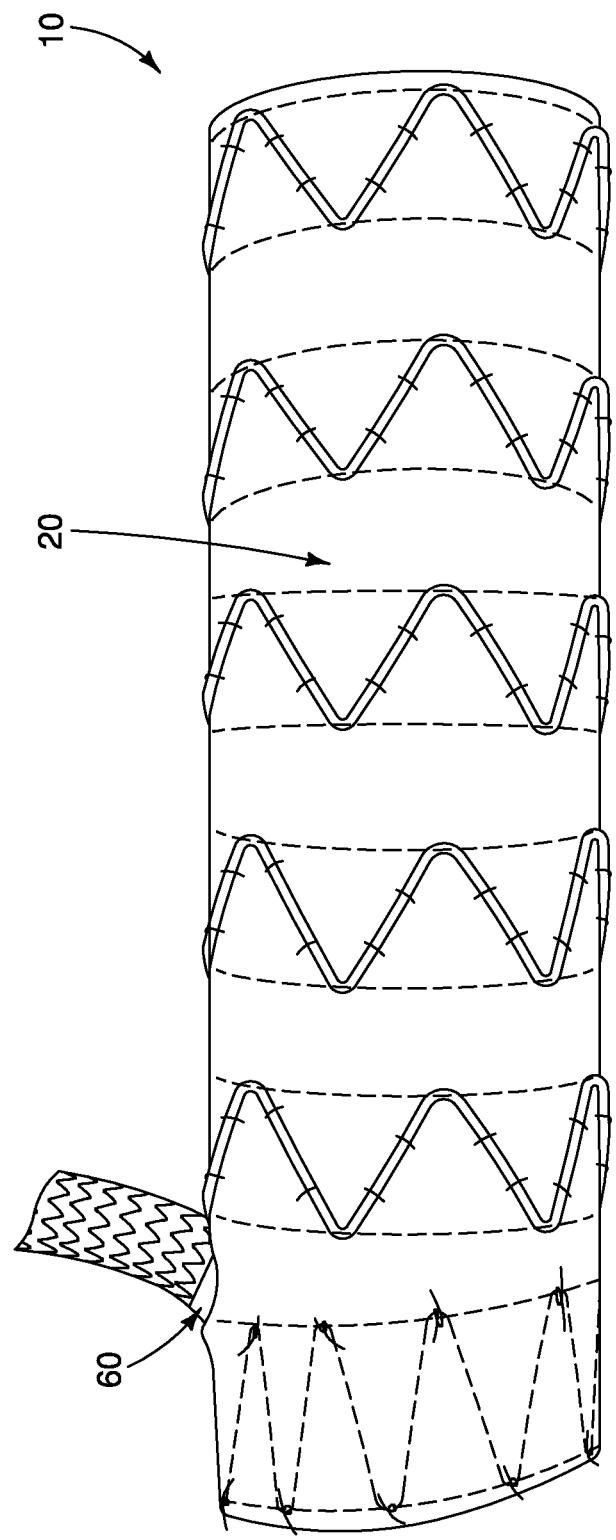
FIG. 27 depicts the endoluminal prosthesis of FIGS. 23-24 with the branch in an antegrade configuration and a branch prosthesis deployed therein.
Figure 28:
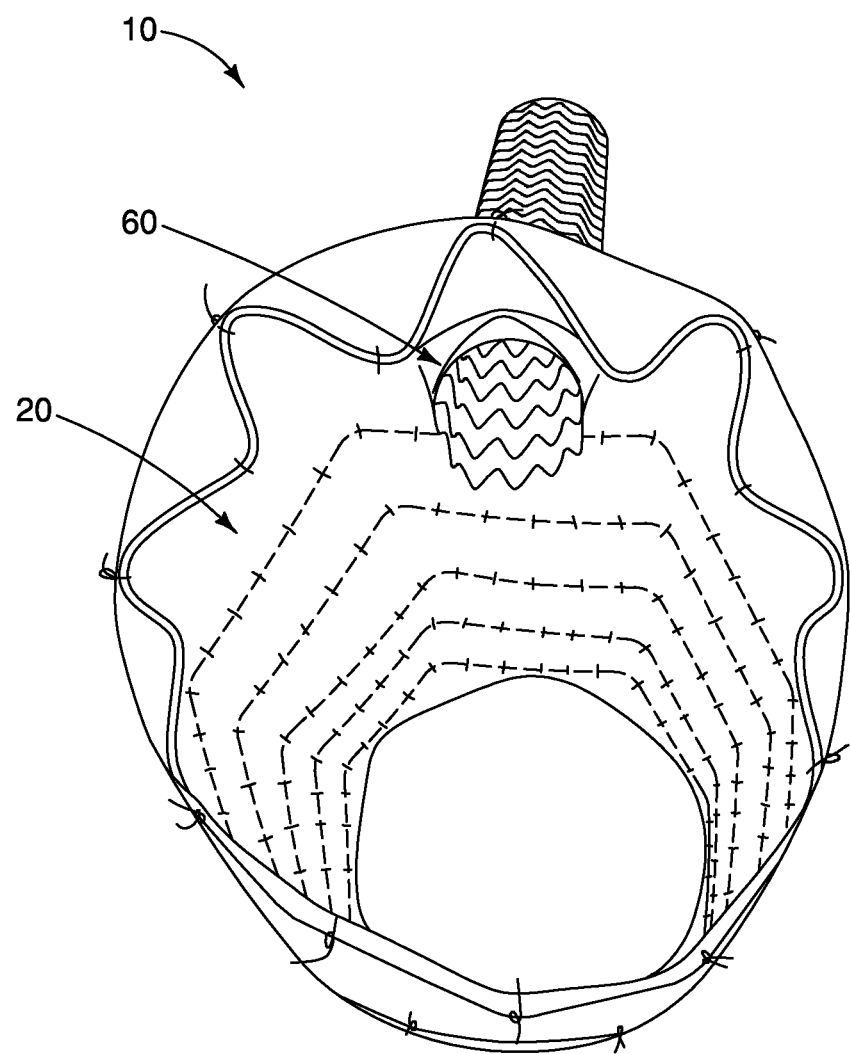
FIG. 28 depicts a lumen of the endoluminal prosthesis of FIGS. 23-24 with a branch prosthesis deployed therein.

The branch 60 may be attached to the graft body 20 adjacent to the slit 29. The position of the branch 60 within the slit 29 may cause a portion of the branch 60 adjacent to the slit to deform. In other words, the portion of the graft body 20 adjacent to the slit 29 may squeeze the branch 60 to deform a portion of the branch. In one example, the deformed portion of the branch 60 adjacent to the slit 29 may have an elliptical shape as shown in FIGS. 23-25. In other examples, the deformed portion of the branch may have any other shape. This may aid in enabling the branch to move or pivot about the slit between the retrograde and antegrade configurations.

The slit may have a length, which may extend circumferentially along the graft body 20. In other examples, the length of the slit may extend longitudinally along the graft body 20, or in any other direction relative to the graft body. The slit may be substantially linear with respect to the surface of the graft body 20. For example, the slit may be configured as a linear slit extending circumferentially along the graft body 20 in a direction transverse to the longitudinal axis of the graft body. Alternatively, the slit may have an arcuate shape or any other suitable shape with respect to the surface of the graft body 20. The length of the slit may be less than or equal to about ½ of the circumference of the branch 60. Additionally, or alternatively, the length of the slit may be greater than or equal to about ⅖ of the circumference of the branch 60. Preferably, the length of the slit may range from about ⅖ of the circumference of the branch 60 to about ½ of the circumference of the branch. In one example, the diameter of the branch 60 may be between about 6 mm and about 14 mm, typically between about 8 mm and about 12 mm. In one example, the diameter of the branch 60 may be about 8 mm (e.g., the branch may be configured as an 8 mm reinforced tube), and the length of the slit may be about 12.5 mm. In one example, the length of the branch 60 may be between about 8 mm and about 15 mm. In other examples, the branch may have any suitable diameter and/or length. Additionally, or alternatively, the size of the slit may be selected according to the diameter of the branch as described above.

The size of the slit relative to the branch 60 may aid in securing the branch to the graft body 20. For example, the length of the slit may be sufficiently small, as compared to the circumference of the branch 60, that the branch is engaged (e.g., frictionally engaged) by the graft body 20 at the slit. The graft material of the graft body 20 may be sufficiently flexible to enable the branch 60 to move generally as described above. The spacing between the adjacent stents may be sufficiently large to enable such flexibility. In other words, an unsupported longitudinal section of the graft material of the graft body 20 between the adjacent stents may be sufficiently flexible to enable movement of the branch. Additionally, or alternatively, the slit may enable movement of the branch 60 relative to the graft body 20. For example, the slit may be configured to enable the graft material of the graft body 20 adjacent to the slit to move (e.g., inward or outward with respect to the longitudinal axis of the graft body). Such movement of the graft material adjacent to the slit may enable movement of the branch 60 as described above. For example, the branch 60 may be configured to pivot about the slit between the retrograde configuration and the antegrade configuration as described above. In this embodiment, the branch may have less of a tendency to sit in the aortic lumen. In one example, the branch may be biased toward one of the retrograde configuration and the antegrade configuration. In other examples, the branch may be substantially unbiased. In other words, the graft material of the graft body 20 may be sufficiently flexible that the graft material does not exert a biasing force on the branch 60. The branch 60 may be disposed partially within the lumen 26 of the prosthesis 10 and partially external to the prosthesis as described above. Alternatively, the branch 60 may be disposed entirely within the lumen 26 of the prosthesis 10 or entirely external to the prosthesis also as described above.

Figure 21:
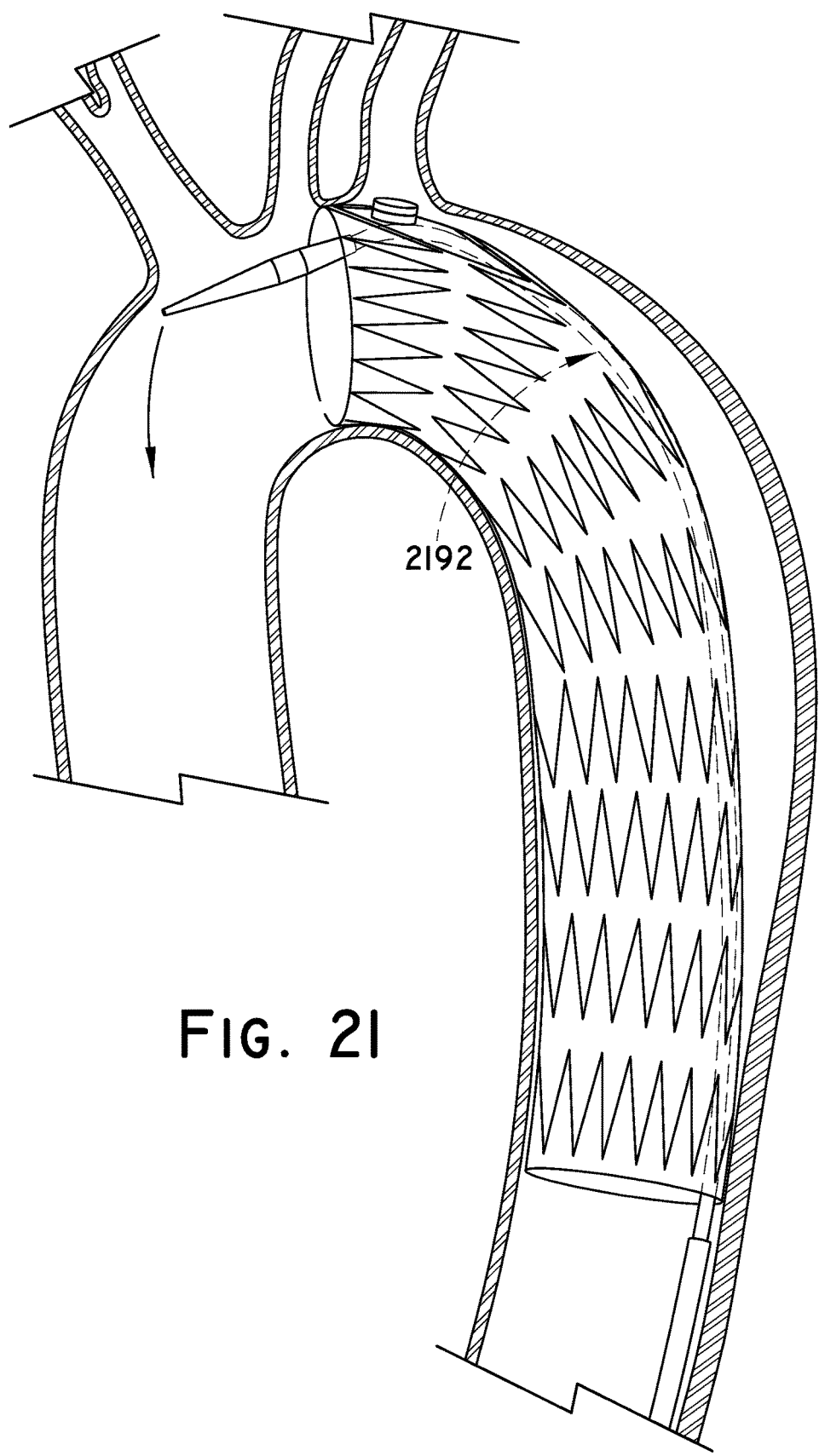
FIG. 21 illustrates one embodiment of an introducer having a curved cannula.

In one example, the branch 60 may be positioned near the proximal end 27 of the graft body 20. For example, the branch 60 may be placed between about 5 mm and about 30 mm, between about 10 mm and about 25 mm, or between about 15 mm and about 20 mm from the proximal end 27 of the graft body 20. Additionally, or alternatively, the graft body 20 may have a length, for example, ranging from about 10 cm to about 200 cm. Additionally, or alternatively, the branch 60 may be spaced from the proximal end 27 of the graft body 20 by between about 0.25% and about 30%, between about 0.5% and about 25%, or between about 0.75% and about 20% of the length of the graft body. The proximity of the branch 60 to the proximal end 27 of the graft body 20 may aid in aligning the branch with a branch vessel (e.g., the subclavian artery) while landing the proximal end of the graft body between two adjacent branch vessels (e.g., the subclavian artery and the carotid artery) without occluding the branch vessels as shown in FIG. 21.

In one example, the branch 60 may remain substantially linear upon movement between the retrograde configuration and the antegrade configuration. In other words, the branch may be movable between the retrograde configuration and the antegrade configuration without bending the branch. The movement or flexibility of the graft material surrounding the branch (e.g., the deformable region or the graft material adjacent to the slit) may enable the branch to move while remaining substantially linear.

Figure 29:
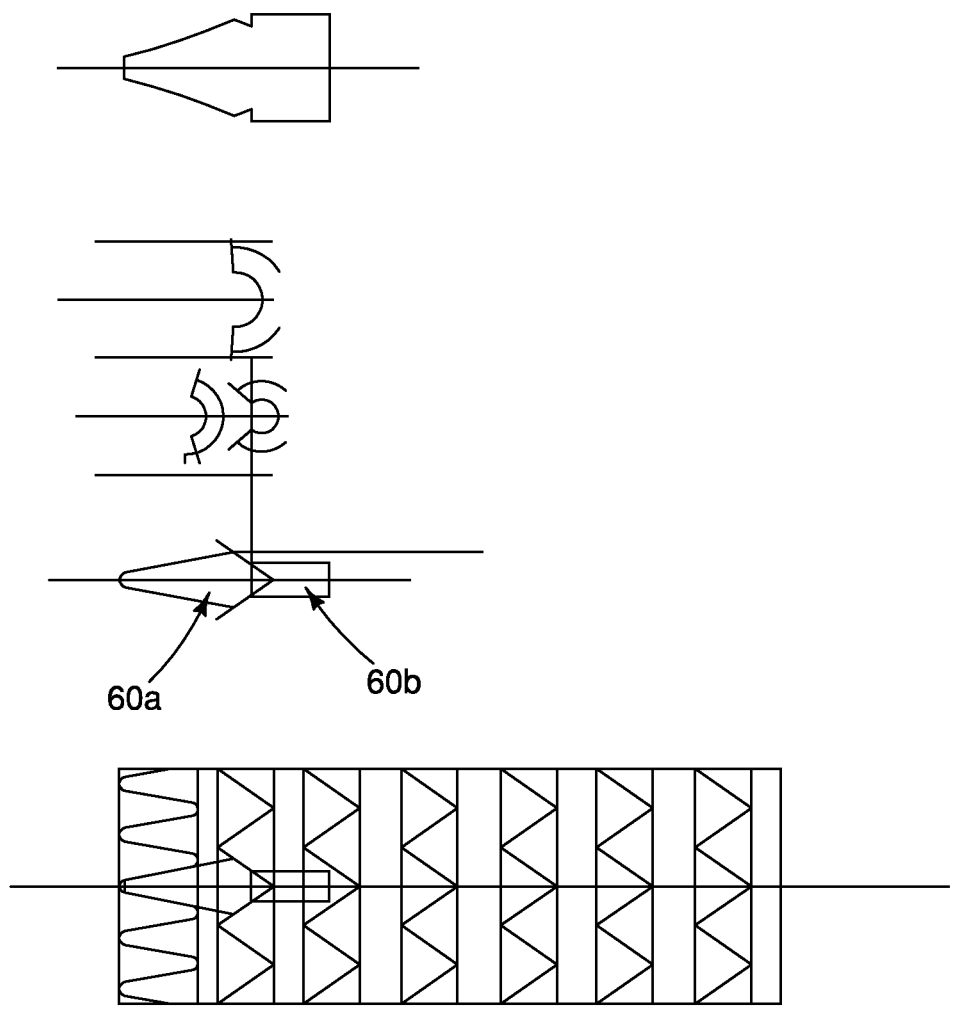
FIGS. 29-30 depict one embodiment of a trough formed in an endoluminal prosthesis and a branch extending from the trough.
Figure 30:
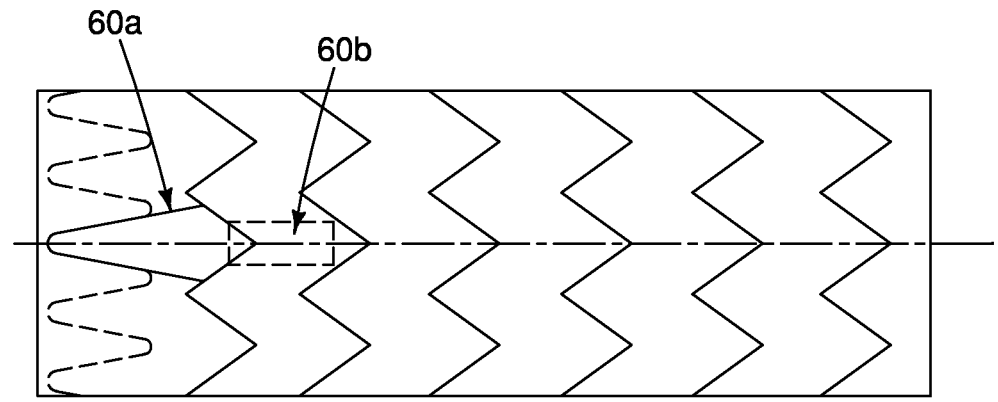
Figure 31:
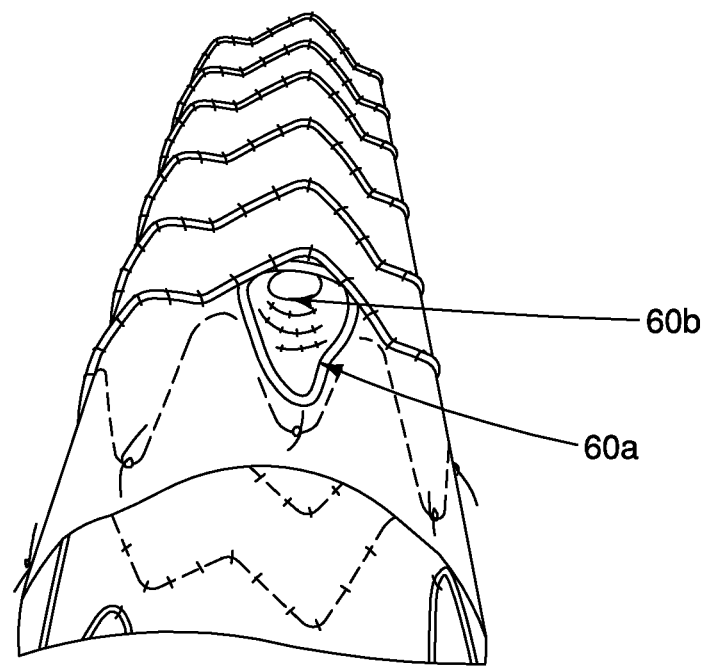
FIGS. 31-32 depict one embodiment of an endoluminal prosthesis having a trough and a branch.

In another embodiment, a prosthesis may include a retrograde branch as shown in FIGS. 29-34. The retrograde branch may include a trough portion 60a and a tubular branch portion 60b. The tubular branch portion may be configured, for example, as a 7 mm×18 mm internal spiral branch. The trough portion and the branch portion may be formed from a piece of graft material as shown in FIG. 29. At least a portion of the piece of graft material may be rolled into a generally tubular shape to form the branch portion. A section of graft material may be removed from a region of the prosthesis positioned between first and second proximal stents of the prosthesis. The region may be substantially diamond shaped as shown in FIGS. 29-34. Alternatively, the region may have any other shape. The branch and trough configuration can be modified to accommodate first and second proximal stents having any configuration. The trough portion may be configured to align generally with the struts of the first and/or second proximal stents. The trough portion of the retrograde branch may be attached to the graft body of the prosthesis along a perimeter of the opening formed in the graft body by removal of the section of graft material. The trough portion may be attached to the graft body of the prosthesis by any suitable method. For example, the trough portion may be stitched to the graft material of the graft body and one or more struts of the first proximal stent using a running blanket stitch as shown in FIGS. 30-34. Alternatively, the trough portion may be formed during weaving of the graft material of the graft body.

Figure 32:
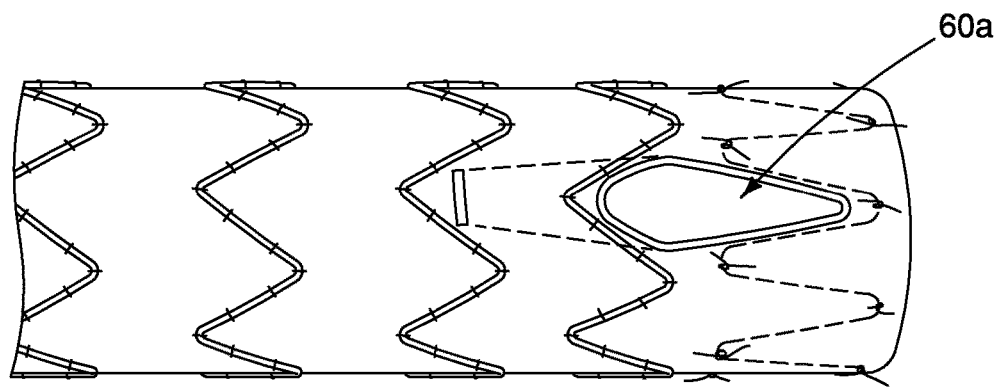
Figure 33:
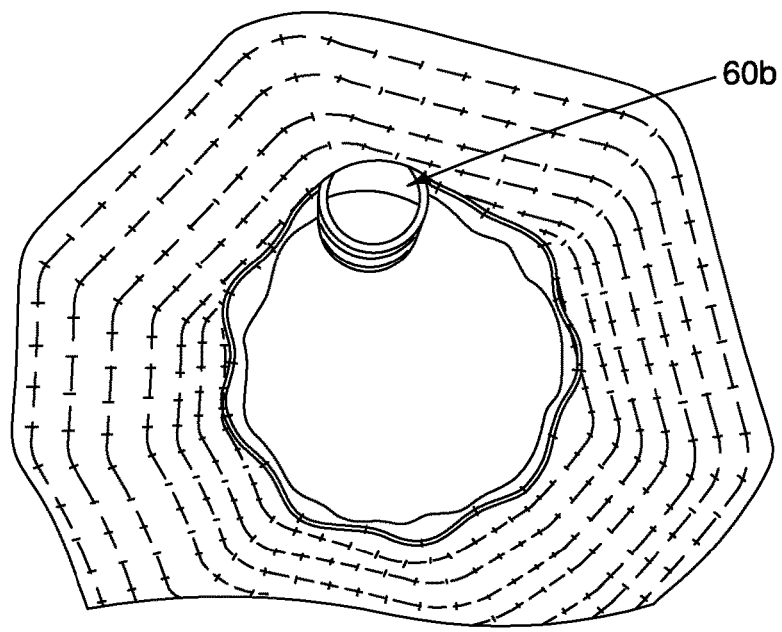
FIG. 33 depicts a lumen of the endoluminal prosthesis of FIGS. 31-32 from a distal end of the prosthesis.
Figure 34:
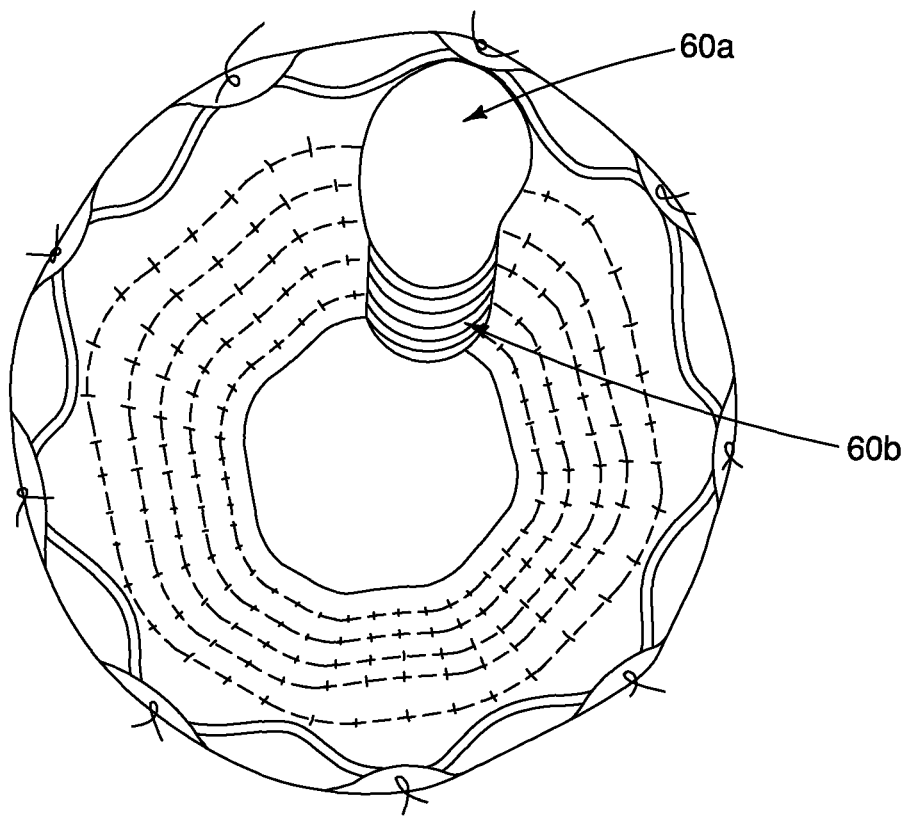
FIG. 34 depicts a lumen of the endoluminal prosthesis of FIGS. 31-32 from a proximal end of the prosthesis.

The trough portion and/or the branch portion may be positioned generally within the lumen of the prosthesis. The branch portion may be attached to (or integral with) and extend from the trough portion. The branch portion may extend in a generally distal direction from the trough portion as shown in FIGS. 29-34 (i.e., the branch portion may be configured as a retrograde branch). Alternatively, the branch portion may extend in a generally proximal direction from the trough (i.e., the branch portion may be configured as an antegrade branch). The end of the branch opposite the trough may be attached to the graft body. For example, the end of the branch may be stitched to the graft body as shown in FIG. 32. This may aid in supporting the branch within the lumen of the prosthesis. For the branch to fit appropriately, the trough design may be customized to fit the branch diameter and/or length. This design may enable a target branch vessel to be perfused in a retrograde manner. This may aid in deploying the prosthesis from a femoral approach.

In any of the examples described herein, movement of the branch 60 relative to the graft body 20 may aid in aligning the branch with a branch vessel such as, for example, the left subclavian artery. For example, the branch 60 may be positioned at different angles relative to the graft body 20 to account for any misalignment between the opening in the deformable region 40 and the branch vessel. If the prosthesis 10 is placed such that the branch 60 is slightly proximal of the ostium of the branch vessel, the branch may be moved into the antegrade configuration to extend generally in the direction of the branch vessel. If the prosthesis 10 is placed such that the branch 60 is slightly distal of the ostium of the branch vessel, the branch may be moved into the retrograde configuration to extend generally in the direction of the branch vessel. In this manner, movement of the branch 60 may compensate for misalignment between the branch 60 and the branch vessel upon deployment of the prosthesis 10.

Such movement of the branch 60 may aid in delivering the prosthesis 10 by several different methods including femoral delivery, brachial delivery, axillary delivery, subclavian delivery, and/or transapical delivery. For example, the prosthesis 10 may be delivered via the femoral artery with the branch 60 in the retrograde position. In the retrograde position, the opening of the second end 68 of the branch 60 may face proximally so that a catheter extending through the branch also may extend proximally. This may aid in cannulating a branch vessel and/or snaring the catheter from the branch vessel when delivering the prosthesis 10 from distal to the branch vessel. In other words, the branch 60 may be oriented in the retrograde configuration to receive a catheter, as further described below, extending generally proximally for delivery of the prosthesis 10 using a retrograde approach (e.g., a femoral approach).

In another example, the prosthesis 10 may be delivered using brachial, axillary, or transapical delivery with the branch 60 in the antegrade position. In the antegrade position, the opening of the second end 68 of the branch 60 may face distally so that a catheter extending through the branch also may extend distally. This may aid in cannulating a branch vessel and/or snaring the catheter from the branch vessel when delivering the prosthesis 10 from proximal to the branch vessel. In other words, the branch 60 may be oriented in the antegrade configuration to receive a catheter, as further described below, extending generally distally for delivery of the prosthesis 10 using an antegrade approach (e.g., a brachial, axillary, or transapical approach). The ability to move the branch 60 relative to the graft body 20 may aid in delivering the prosthesis 10 from distal or proximal to a target branch vessel (e.g., using a retrograde or an antegrade approach). The opening of the second end 68 of the branch 60, and thus the catheter extending through the branch, may be directed proximally or distally to face the branch vessel regardless of whether the prosthesis 10 is delivered from distal or proximal to the branch vessel. Thus, the same prosthesis may be used regardless of the delivery approach selected by the physician.

A common practice in treating patients with Type B dissection with conventional endografts is to use a through wire starting from the subclavian artery, snaring the wire, and pulling the wire out the femoral artery. In this way, the subclavian approach is used to facilitate cannulation of the true lumen, yet allow delivery of the device from the femoral approach. A transapical approach would also have similar benefits. Specific delivery system modifications (e.g., the location of the cannula, the location of preloaded catheters, the orientation of the device, the length of the tip, etc.) may exist for each delivery paradigm.

The prosthesis 10 may be sized and shaped for placement within the vasculature of a patient as further described below. The preferred size and shape of the prosthesis 10 depends on the anatomy in which it is to be implanted. Physiological variables, deployment characteristics, and other factors also may contribute to the determination of a proper size and shape of the prosthesis 10. For example, the prosthesis 10 may have a size and shape suitable for placement in the aortic arch, and/or the descending aorta. To that end, the prosthesis 10 may be configured for placement within the thoracic aorta with the proximal end 27 being placed in the aortic arch and the distal end 28 being placed in the descending aorta. The branch 60 may be configured to align with a branch vessel such as the left subclavian artery. The graft body 20 may have a diameter, for example, ranging from about 10 mm to about 50 mm, typically from about 22 mm to about 46 mm. The diameter of the graft body 20 may be constant along the length thereof. Alternatively, the graft body 20 may be tapered such that the diameter of the graft body may vary along the length thereof. For example, the diameter of the graft body 20 may taper from a larger diameter to a smaller diameter in a proximal to distal direction. In one example, the graft body 20 may have a proximal to distal taper of up to about 10 mm. A tapered graft body 20 may be advantageous for placement within a narrowed aorta. Such a narrowed aorta may be common when treating aortic dissection. The branch 60 may have a diameter, for example, ranging from about 6 mm to about 24 mm, typically from about 8 mm to about 12 mm. The diameter of the branch 60 may be constant along the length thereof. Alternatively, the branch 60 may be tapered such that the diameter of the branch may vary along the length thereof. The prosthesis 10 may be deployed in combination with various other prostheses to effectively bridge an aneurysmal and/or dissected portion of the vasculature.

It is further contemplated that a prosthesis may have multiple deformable regions and/or multiple branches. For example, the prosthesis may have two, three, or more branches attached to one or more deformable regions positioned on the graft body. The various deformable regions and/or branches may be positioned at different longitudinal and circumferential positions along the graft body. In this manner, the branches may be configured to align with, for example, the left subclavian, left common carotid, and/or inanimate arteries. Additionally, or alternatively, the prosthesis may be configured for placement at various other positions within the vasculature of the patient.

One or more radiopaque markers may be included to provide radiographic visualization of the position of the prosthesis 10 when placed in a body vessel of a patient. A plurality of radiopaque markers, which according to one example may be provided in the form of gold beads, may be coupled to the graft body 20 (e.g., the graft material 22 and/or the support structure 30), the deformable region 40 (e.g., the graft material 42 and/or the perimeter 46), and/or the branch 60 (e.g., the graft material 62 and/or the support structure 70) to facilitate imaging of various desired locations along the length of the prosthesis 10. The radiopaque markers may be positioned at the proximal end 27 and/or the distal end 28 of the graft body 20. The radiopaque markers also may be positioned proximate the deformable region 40 and/or the branch 60 to facilitate proper alignment with a branch vessel.

The prosthesis 10 may be provided as part of a preloaded system as shown in FIG. 2. The preloaded system may include a catheter 82, which may be configured to facilitate cannulation of a branch vessel, movement of the branch 60, and/or insertion of a branch prosthesis within the branch 60. The catheter 82 may be preloaded in the prosthesis 10 prior to introduction of the prosthesis within a patient. When preloaded as part of a delivery system, a proximal region 84 of the catheter 82 may be advanced through the lumen 26 of the graft body 20 from the distal end 28 toward the proximal end 27. The proximal region 84 of the catheter 82 then may be advanced through the branch 60 to exit the prosthesis 10 as shown in FIG. 2. This configuration of the preloaded catheter 82 (i.e., extending proximally within the prosthesis 10 from the distal end 28) may be desirable for retrograde delivery of the prosthesis (e.g., femoral delivery). In other examples, the catheter 82 may be advanced through the lumen 26 from the proximal end 27 toward the distal end 28. This configuration of the preloaded catheter 82 (i.e., extending distally within the prosthesis 10 from the proximal end 27) may be desirable for antegrade delivery of the prosthesis (e.g., brachial, axillary, or transapical delivery). The catheter 82 may sit in a separate groove in a tip of a delivery device. Pulling back a sheath may expose the catheter 82 to allow a physician to snare and withdraw the preloaded catheter through a sheath in the subclavian artery as further described below. The catheter 82 may include a catch member such as a hook, loop, or eye at the proximal region 84 to aid the physician in snaring the catheter. Additionally, or alternatively, a guidewire may be received within a lumen of the catheter 82. The guidewire may be preloaded in the prosthesis as described above with respect to the catheter 82 and/or received within the preloaded catheter. The guidewire may facilitate the placement of various other instruments, devices, or components (e.g., the balloon described below) within the vasculature of the patient.

Various stent configurations may be used, particularly for the proximal stents, to provide a low profile prosthesis and to limit graft infolding between stent points. Low profile (e.g., about 0.125 mm thick) or ultra low profile (e.g., about 0.080 mm thick) graft material and/or selected stent configurations may provide for a delivery system diameter ranging from about 12 to about 20 Fr for a prosthesis having a diameter ranging from about 28 to about 46 mm. For example, sheath sizes of about 18 to about 20 Fr may be possible for a 38 mm device manufactured from low profile materials, and sheath sizes of about 14 to about 16 Fr may be possible for a 38 mm device manufactured from ultra low profile materials. Delivery system sizes of approximately 18 Fr or smaller may enable delivery from the subclavian artery in some patients. Placement of a guidewire in the true lumen when treating Type B dissection may be simplified by using subclavian delivery as opposed to femoral delivery. The ability to change the orientation of the branch 60 relative to the graft body 20 also may aid in delivering the prosthesis 10 via the subclavian artery (or any other forms of delivery as described above).

Several examples of proximal stent configurations are shown in FIGS. 6-11. Generally, reducing the number of stent points may increase the outward radial force provided by a prosthesis and/or reduce the profile of a prosthesis, but also may create relatively large flaps of graft material between the stent points. This may increase the likelihood of a Type I endoleak. Therefore, multiple stents may be placed proximate the proximal end of the graft body to provide a combination of outward radial force and limited graft infolding.

Figure 7:
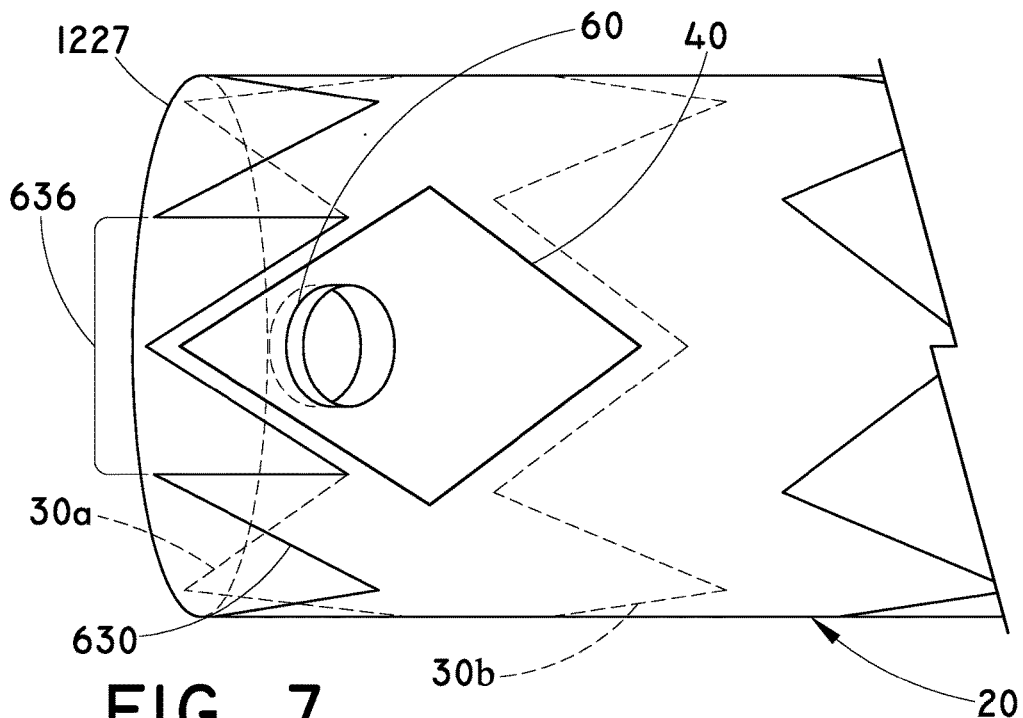
FIGS. 6-11 illustrate various embodiments of stent configurations for use on an endoluminal prosthesis.

In one example, the prosthesis 10 may include a third proximal stent 630 as shown in FIGS. 6-7. The first proximal stent 30a may be positioned on the inner surface 23 of the graft material 22 proximate the proximal end 27 of the graft body 20 as described above. The third proximal stent 630 may be positioned on the outer surface 24 of the graft material 22 proximate the proximal end 27 of the graft body 20. The third proximal stent 630 may be generally longitudinally aligned with the first proximal stent 30a. In other words, the third proximal stent 630 and the first proximal stent 30a may at least partially overlap one another on opposing surfaces of the graft material 22 of the graft body 20. The third proximal stent 630 may have a length or amplitude that is substantially the same as the length or amplitude of the first proximal stent 30a. The third proximal stent 630 may be generally circumferentially misaligned with the first proximal stent 30a such that the peaks of the first proximal stent are generally aligned with the valleys of the third proximal stent and vice versa as best illustrated in FIG. 6. The third proximal stent 630 may include an irregular circumferential portion 636 as shown in FIG. 7. The irregular portion 636 may be aligned circumferentially with the deformable region 40 and may include an additional peak. In other words, the stent pattern of the third proximal stent 630 may be disrupted in the irregular portion 636 to include an additional peak such that the third proximal stent may include one more peak than the first proximal stent 30a. The additional peak of the third proximal stent 630 may be generally aligned with the peak 32a of the first proximal stent 30a in alignment with the deformable region 40 and/or the branch 60. The additional peak of the third proximal stent 630 may replace the valley of the third proximal stent that may otherwise extend into the deformable region 40. In this manner, the irregular portion 636 may modify the stent pattern of the third proximal stent 640 so that the third proximal stent remains outside of the deformable region 40.

In this example, the first proximal stent 30a may provide a majority of the outward radial force for sealing the prosthesis 10 against the wall of the body vessel. Because a majority of the outward radial force may be applied by the first proximal stent 30a, the third proximal stent may be configured to apply a relatively small amount of outward radial force. Thus, the third proximal stent 630 may be formed from a wire having a smaller diameter or cross sectional area than that of the first proximal stent 30a. The third proximal stent 630 may limit graft infolding between the peaks of the first proximal stent 30a and/or the third proximal stent. The misalignment between the peaks of the first and third proximal stents 30a, 630 may reduce the unsupported circumferential lengths of graft material 22 along the proximal end 27 of the graft body 20. The shorter circumferential lengths of unsupported graft material 22 may be less likely to fold inward, thus reducing the likelihood of endoleak.

This stent configuration, or other stent configurations described herein, may limit graft infolding while providing a reduced outward radial force. The limited graft infolding may be achieved by the additional stent points which may reduce the unsupported circumferential lengths of graft material. The reduced outward radial force may be achieved by reducing the outward radial force applied by the third proximal stent (e.g., by the smaller cross sectional area of the wire used to form the third proximal stent). Such a combination of reduced outward radial force and limited graft infolding may be desirable for treatment of an aortic dissection. For example, this stent configuration may provide adequate graft apposition to the aortic wall (e.g., sufficient outward radial force) to ensure coverage of the true/false lumen communication. The reduced outward radial force applied by the prosthesis may reduce the probability of retrograde dissection. In other words, the outward radial force provided by the prosthesis may be sufficiently large for graft apposition to the aortic wall but sufficiently small to reduce the probability of retrograde dissection.

Figure 9:
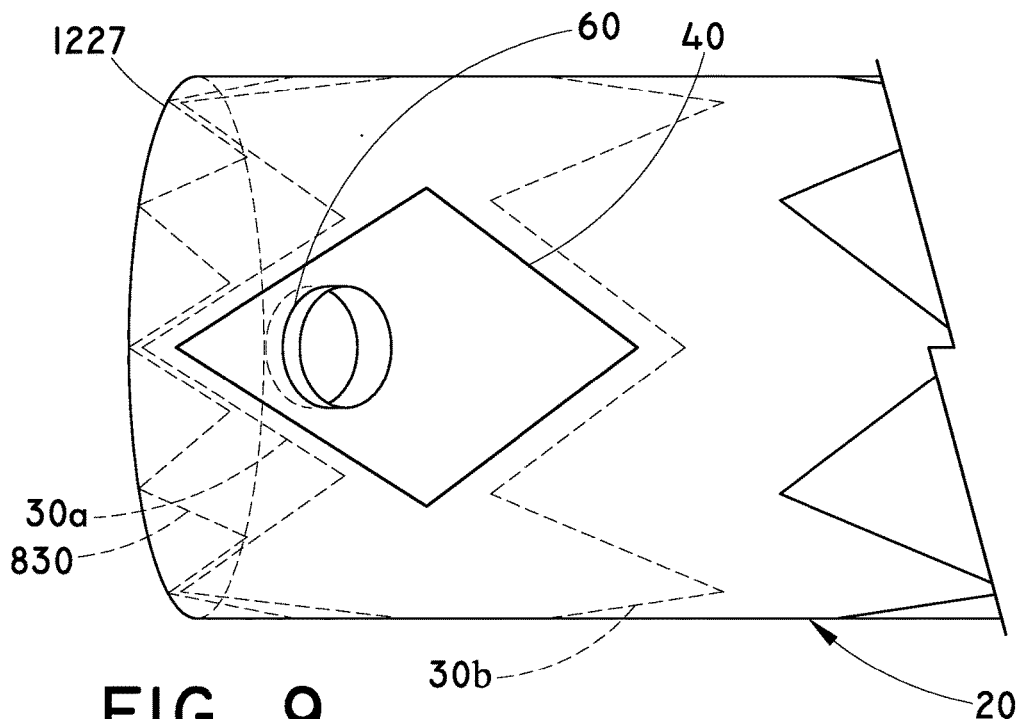

In another example, the prosthesis 10 may include a third proximal stent 830 as shown in FIGS. 8-9. The first proximal stent 30a may be positioned on the inner surface 23 of the graft material 22 proximate the proximal end 27 of the graft body 20 as described above. The third proximal stent 830 may be positioned on the inner surface 23 of the graft material 22 proximate the proximal end 27 of the graft body 20. The third proximal stent 830 may be positioned proximal of the first proximal stent 30a and may have a length, or amplitude, that is less than the length of the first proximal stent. In other words, the first proximal stent 30a and the third proximal stent 830 may have dissimilar lengths. The first proximal stent 30a and the third proximal stent 830 may be arranged in a nested relationship with one another such that no portion of the third proximal stent may overlap any portion of the first proximal stent. The third proximal stent 830 may include twice as many peaks and valleys as the first proximal stent 30a. Every other peak of the third proximal stent 830 may be generally circumferentially aligned with a peak of the first proximal stent 30a. In this manner, the third proximal stent 830 may increase the number of stent points or peaks provided circumferentially along the proximal end 27 of the graft body 20 while remaining outside of the deformable region 40. The third proximal stent 830 may have any number of peaks and valleys, and is not limited to having twice as many peaks and valleys as the first proximal stent 30a. Preferably, the third proximal stent 830 may have a greater number of peaks than the first proximal stent 30a to limit graft infolding as described herein.

In this example, the first proximal stent 30a may provide a majority of the outward radial force for sealing the prosthesis 10 against the wall of the body vessel. The third proximal stent 830 may limit graft infolding between the peaks of the first proximal stent 30a and/or the third proximal stent. To that end, the third proximal stent 830 may be formed from a wire having a smaller diameter or cross sectional area than that of the first proximal stent 30a. The increased number of stent points or peaks that may be provided by the third proximal stent 830 may reduce the unsupported circumferential lengths of graft material 22 along the proximal end 27 of the graft body 20. The shorter circumferential lengths of unsupported graft material 22 may be less likely to fold inward, thus reducing the likelihood of endoleak.

Figure 11:
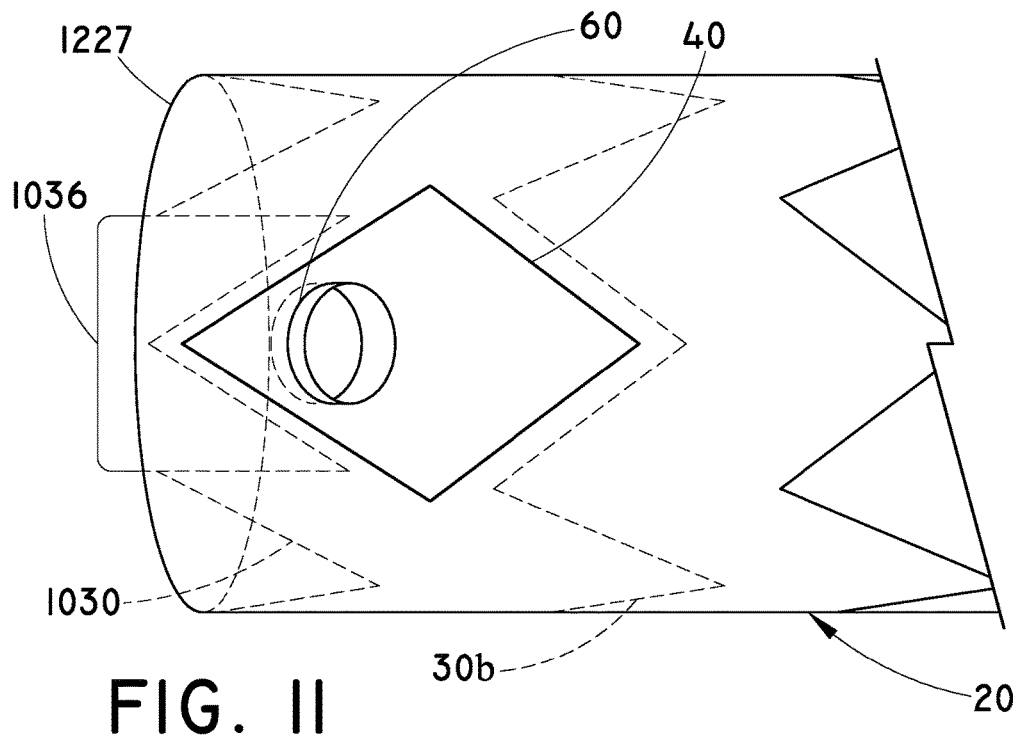

In yet another example, the prosthesis may include a proximal stent 1030 as shown in FIGS. 10-11. The proximal stent 1030 may be positioned on the inner surface 23 of the graft material 22 proximate the proximal end 27 of the graft body 20. The proximal stent 1030 may be included instead of the first proximal stent 30a as shown in FIGS. 10-11. Alternatively, the proximal stent 1030 may be included in addition to the first proximal stent 30a. The proximal stent 1030 may include an increased number of peaks and valleys relative to the first proximal stent 30a. The proximal stent 1030 may include an irregular circumferential portion 1036 as shown in FIG. 11. The irregular portion 1036 may be aligned circumferentially with the deformable region 40 and/or the branch 60. Additionally, or alternatively, the irregular portion 1036 may include a widened peak. In other words, the stent pattern of the proximal stent 1030 may be disrupted (e.g., by removing a peak) in the irregular portion 1036 to include a widened peak. The bend of the widened peak may include an angle that is greater than the angles of the bends of the other peaks of the proximal stent 1030. The widened peak of the proximal stent 1030 may be generally aligned with the deformable region 40 and/or the branch 60. In this manner, the irregular portion 1036 may modify the stent pattern of the proximal stent 1030 so that the proximal stent 1030 remains outside of the deformable region 40.

In this example, the proximal stent 1030 may provide the outward radial force for sealing the prosthesis 10 against the wall of the body vessel. The proximal stent 1030 also may limit graft infolding between the peaks thereof. To that end, the additional stent points or peaks that may be provided by the proximal stent 1030 may reduce the unsupported circumferential lengths of graft material 22 along the proximal end 27 of the graft body 20. The shorter circumferential lengths of unsupported graft material 22 may be less likely to fold inward, thus reducing the likelihood of endoleak.

Figure 13:
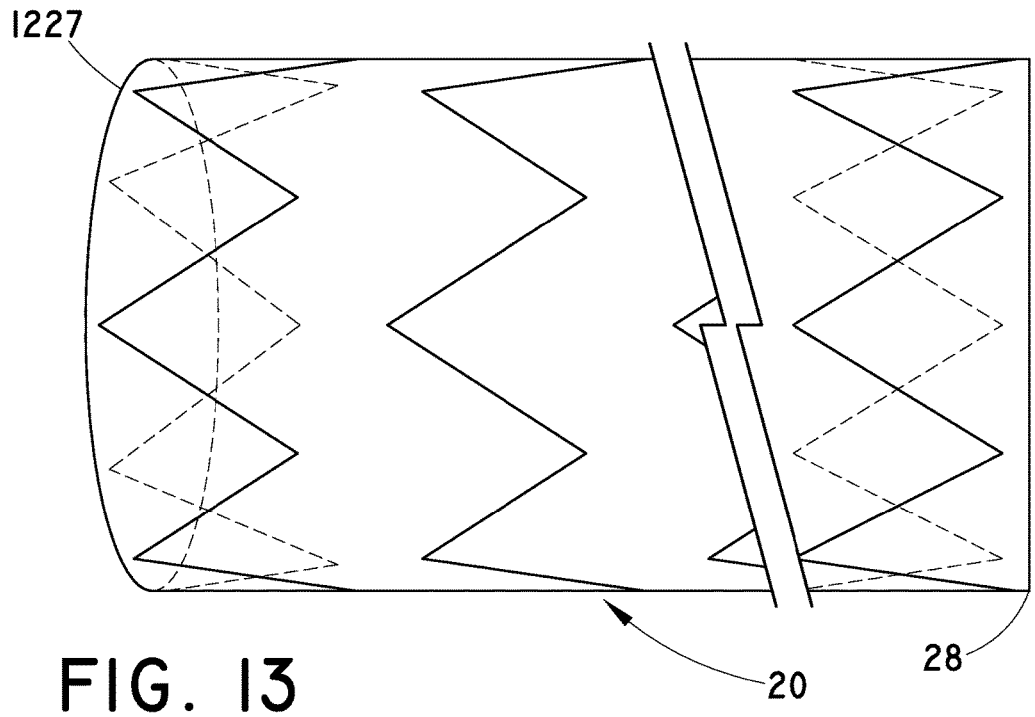
FIGS. 12-13 illustrate a side view and a top view, respectively, of one embodiment of an endoluminal prosthesis having one exemplary stent configuration and a slanted proximal end.
Figure 12:
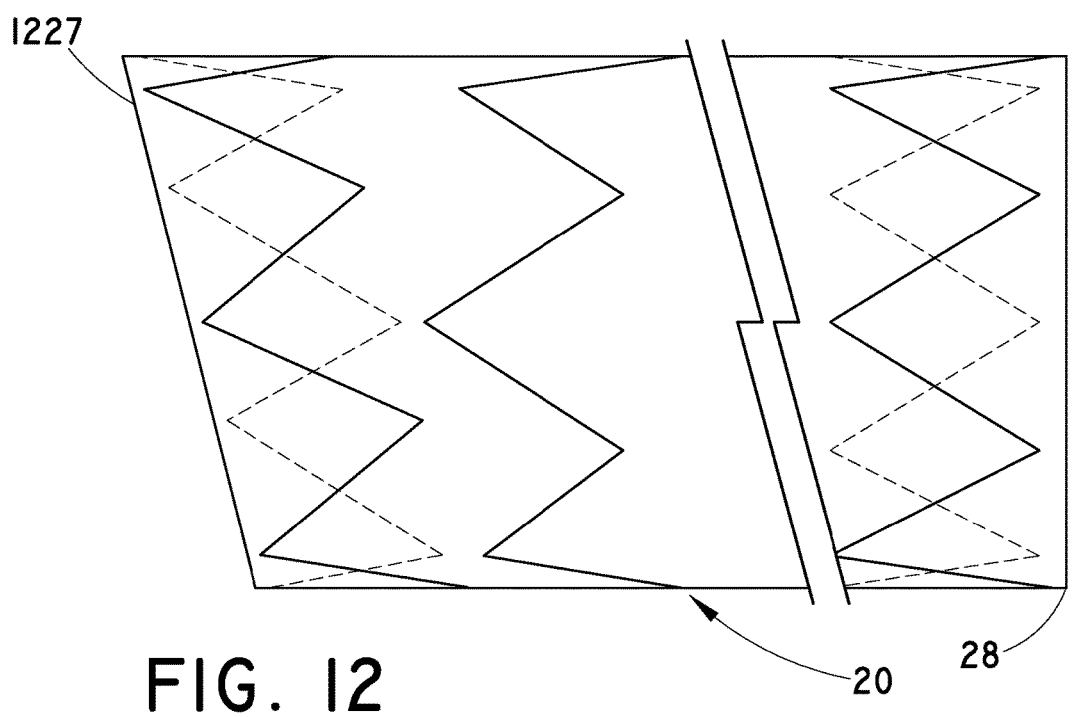
Figure 15:
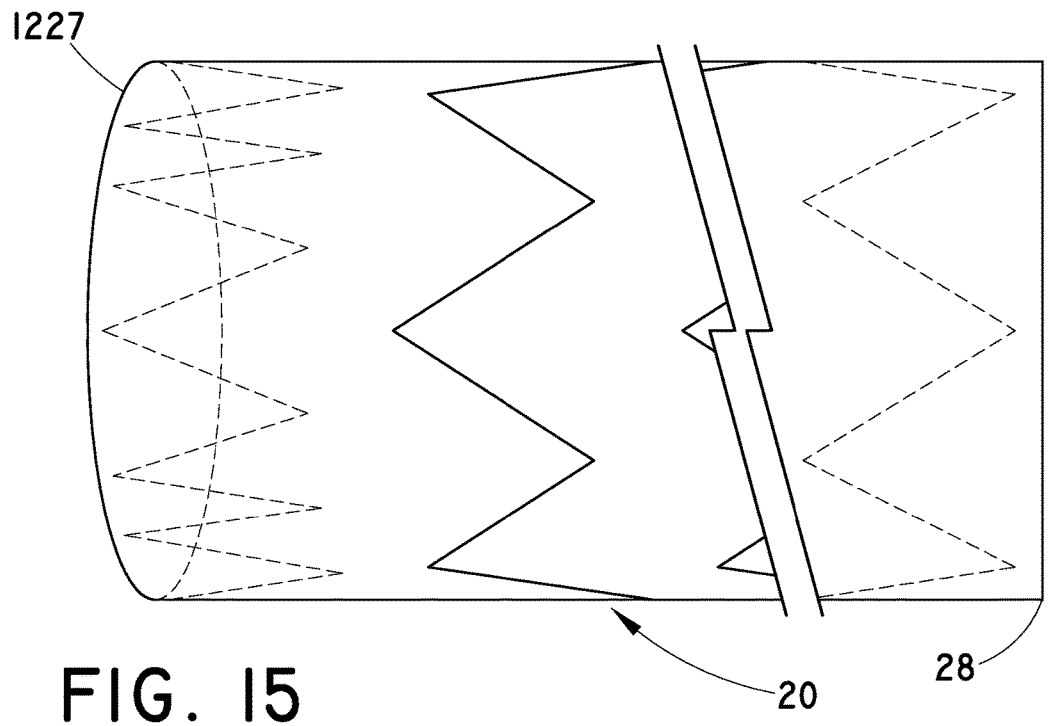
FIGS. 14-15 illustrate a side view and a top view, respectively, of one embodiment of an endoluminal prosthesis having one exemplary stent configuration and a slanted proximal end.
Figure 14:
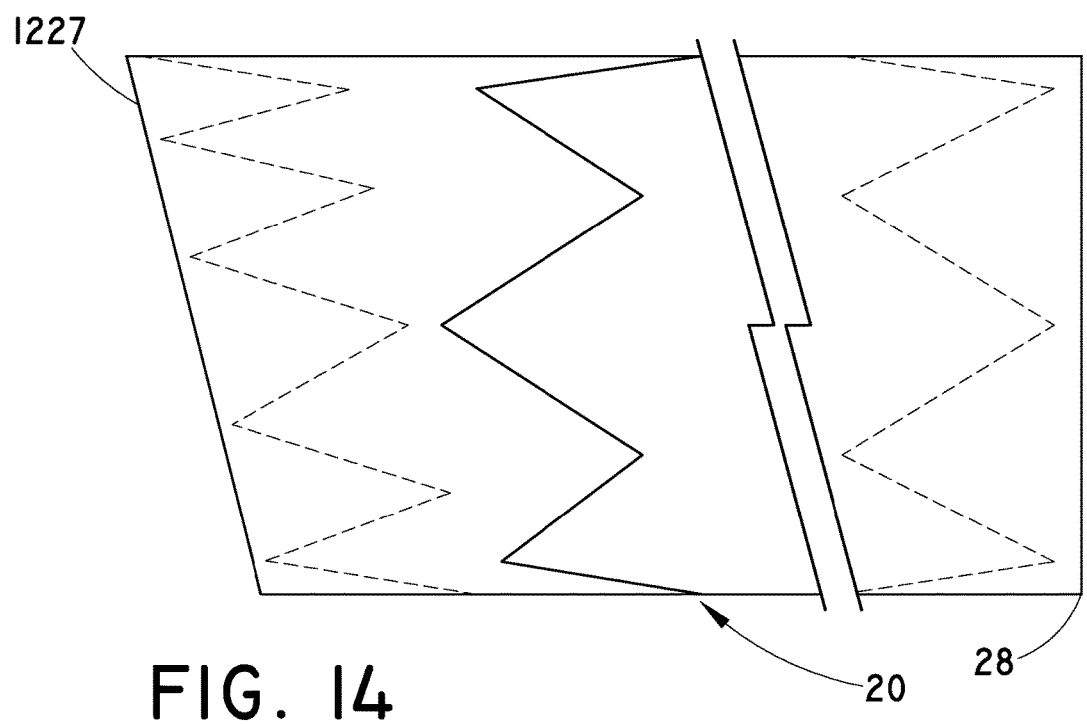

The stent configurations described above, or variations or combinations thereof, may be used at the proximal and/or distal ends of the graft body 20. For example, multiple stents having similar lengths and being misaligned relative to one another may be attached to the proximal end 27 and/or the distal end 28 of the graft body 20 as shown in FIGS. 12-13. The stents may or may not include an irregular circumferential portion as described above. The stent configurations described herein may be particularly beneficial for treating a dissected body vessel. For example, the stent configurations may provide adequate graft apposition to the aortic wall, ensuring coverage of the true/false lumen communication of a dissected aorta. In some examples, the stent configurations also may apply a reduced radial force as compared to conventional stent grafts. This reduced outward radial force may reduce the probability of retrograde dissection.

In the embodiments illustrated in FIGS. 6-15, the graft body 20 of the prosthesis 10 may include a skewed or slanted proximal end 1227. Although not shown in FIGS. 12-15, any of these embodiments may include the deformable region 40 and/or the branch 60 as described herein. A top longitudinal length of the graft body 20 may be longer than a bottom longitudinal length of the graft body to form the slanted proximal end 1227. The top and bottom longitudinal lengths of the graft body 20 may extend generally longitudinally between the proximal end 1227 and the distal end 28 of the graft body and may be separated from one another by approximately 180 degrees around the circumference of the graft body.

At least a portion of the top longitudinal length of the graft body 20 may be configured for placement along the outer curvature of the aortic arch (e.g., the longer portion of the aortic arch). At least a portion of the bottom longitudinal length of the graft body 20 may be configured for placement along the inner curvature of the aortic arch (e.g., the shorter portion of the aortic arch). In other words, the shortest edge of the device may be placed on the inner curve of the aortic arch and the longest edge of the device may be placed on the outer curve of the aortic arch. Aligning the longer length of the graft body 20 with the longer outer curve of the aortic arch and the shorter length of the graft body with the shorter inner curve of the aortic arch may enhance the ability of the prosthesis 10 to conform to the aortic anatomy upon deployment. Such enhanced conformance may enable precise, accurate placement of the prosthesis 10 even in tortuous aortic anatomies.

The prosthesis 10 may be compressed into a delivery configuration and mounted onto a deployment device such as an introducer. Any type of deployment device suitable for deploying a branched stent graft may be used. For example, suitable deployment devices may include those described in U.S. Pat. Nos. 7,488,344 and 7,537,606 to Hartley et al.; U.S. Pat. No. 7,611,529 to Greenberg et al.; and U.S. Patent App. Pub. No. 2009/0204198 by Jensen et al.; which are incorporated by reference herein in their entirety. Although the following description will generally refer to femoral delivery of the prosthesis 10, the prosthesis 10 also may be delivered via subclavian delivery, brachial delivery, transapical delivery, axillary delivery, or any other desirable form of delivery. A person having ordinary skill in the art will appreciate that the configuration and/or orientation of the prosthesis, the delivery device, the preloaded catheter, and/or any components thereof may be modified depending on the chosen delivery method. Such modifications are within the scope of this disclosure.

The prosthesis 10 may be radially compressed into the delivery configuration on a delivery catheter and covered by an outer sheath. To deploy the prosthesis 10, the operator may slide or retract the outer sheath over the delivery catheter, thereby exposing the prosthesis. The prosthesis may expand outwardly upon removal of the sheath. The operator may directly manipulate the introducer, which may provide the operator with a relatively high degree of control during the procedure. Further, such deployment devices may be compact and may have a relatively uniform, low-diameter radial profile, allowing for atraumatic access and delivery.

Using such a suitable delivery system, a physician may introduce the prosthesis 10 in the delivery configuration into the femoral artery and guide the prosthesis into position within the aortic arch and/or the descending aorta. The prosthesis 10 may be positioned using the radiopaque markers such that the branch 60 is generally aligned in the vicinity of the ostium of the left subclavian artery. The sheath of the delivery system, which may constrain the prosthesis 10 in the delivery configuration, may be retracted distally to allow the prosthesis to expand from the delivery configuration.

The prosthesis 10 may remain at least partially restrained in a reduced diameter configuration, for example, by one or more diameter reducing ties. Diameter reducing ties may be applied to the support structure 30 of the graft body 20.

Preferably, diameter reducing ties may be applied to the proximal and distal stents of the graft body 20 to retain the proximal and distal ends 27, 28 in a reduced diameter configuration after retraction of the sheath. This may enable repositioning and/or adjustment of the prosthesis 10 prior to complete expansion of the graft body 20, which may fix the prosthesis in place relative to the vessel wall. In one example, the diameter reducing ties may be configured as threads looped around struts of a stent and a trigger wire. Each thread may be pulled tight to draw the struts of the stent corresponding to that thread closer to one another. The ends of the thread may be tied together and knotted to retain the struts in place relative to the trigger wire, thereby reducing the diameter of the stent. The struts may be released upon removal of the trigger wire to allow expansion of the stent. The diameter reducing ties also may be configured as any other type of constraining member capable of reducing the diameter of a stent of the prosthesis 10. For example, the diameter reducing ties may be configured as described in U.S. Patent App. Pub. No. 2008/0294234 by Hartley et al., which is incorporated by reference herein in its entirety.

Retraction of the sheath also may expose the preloaded catheter 82 extending from the branch 60 as shown in FIG. 2. The catheter 82 may be snared and pulled though a sheath positioned within the left subclavian artery as shown in FIG. 3. A balloon may be tracked over the catheter 82 and positioned within the branch 60 as shown in FIGS. 4-5. The balloon may be manipulated to adjust the orientation of the branch 60 relative to the graft body 20. In one example, a first end of the balloon may be positioned within the lumen 26 of the prosthesis 10. The first end of the balloon may be moved proximally and/or distally relative to the prosthesis 10. Distal movement of the first end of the balloon may cause the branch 60 to move toward the retrograde configuration as shown in FIG. 4. Proximal movement of the first end of the balloon may cause the branch 60 to move toward the antegrade configuration as shown in FIG. 5. Additionally, or alternatively, a second end of the balloon positioned external to the prosthesis 10 may be manipulated to adjust the orientation of the branch 60 relative to the graft body 20. In another example, a catheter associated with the balloon may be manipulated (e.g., advanced, retracted, rotated, or bent) to adjust the orientation of the balloon, and thus the orientation of the branch 60, with respect to the graft body 20. The presence of the inflated balloon within the branch 60 may provide structural stability to the branch and/or maintain patency of the branch during adjustment. The branch 60 may be moved to the retrograde configuration, the antegrade configuration, or any other orientation with respect to the graft body 20, e.g., by manipulating the balloon. The orientation of the branch 60 may be adjusted to align the branch with the left subclavian artery. Additionally, or alternatively, the orientation of the branch 60 may be adjusted to a desired position based on factors such as, for example, the native anatomy, plans for later intervention (e.g., ability to easily access the descending thoracic aorta), or any other relevant factors.

Figure 16:
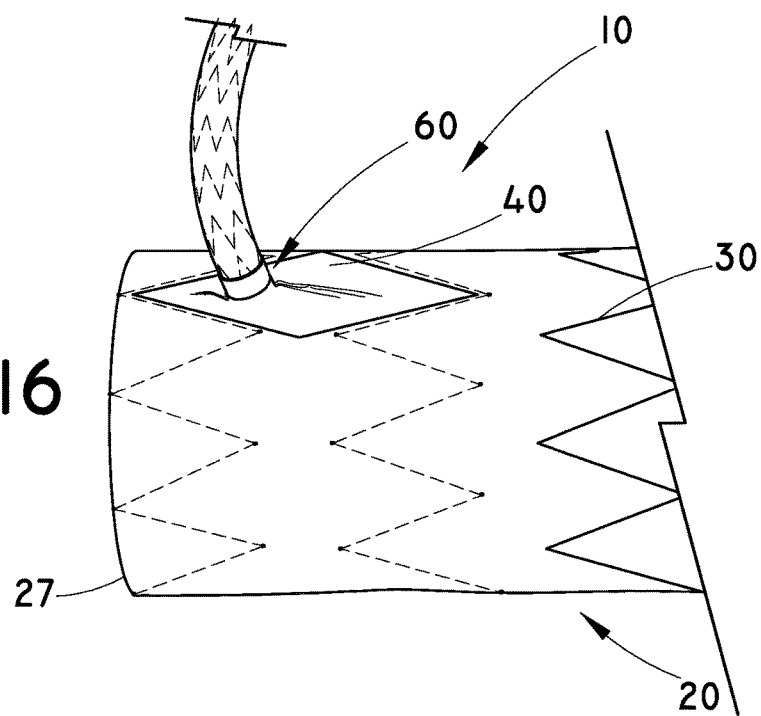
FIGS. 16-17 are perspective views of one embodiment of an endoluminal prosthesis with a branch prosthesis deployed therein.
Figure 17:
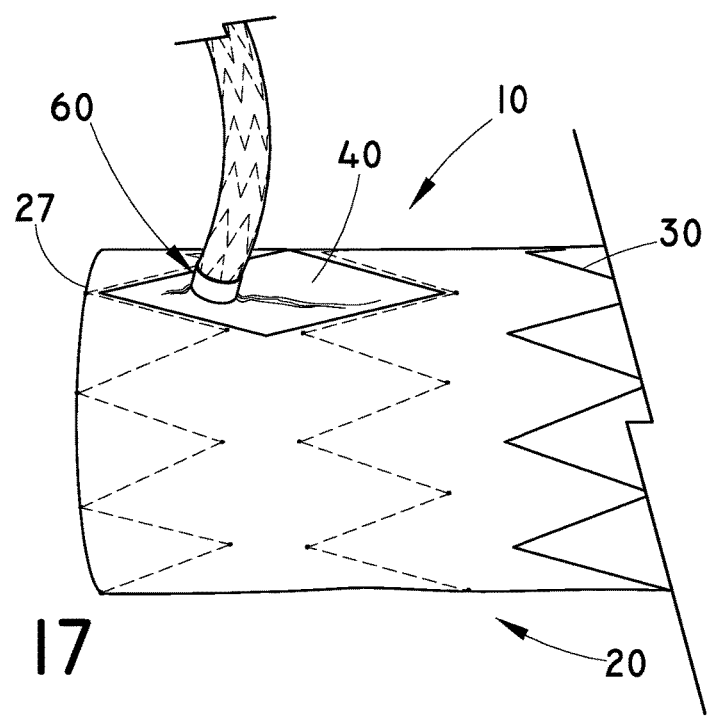
Figure 18:
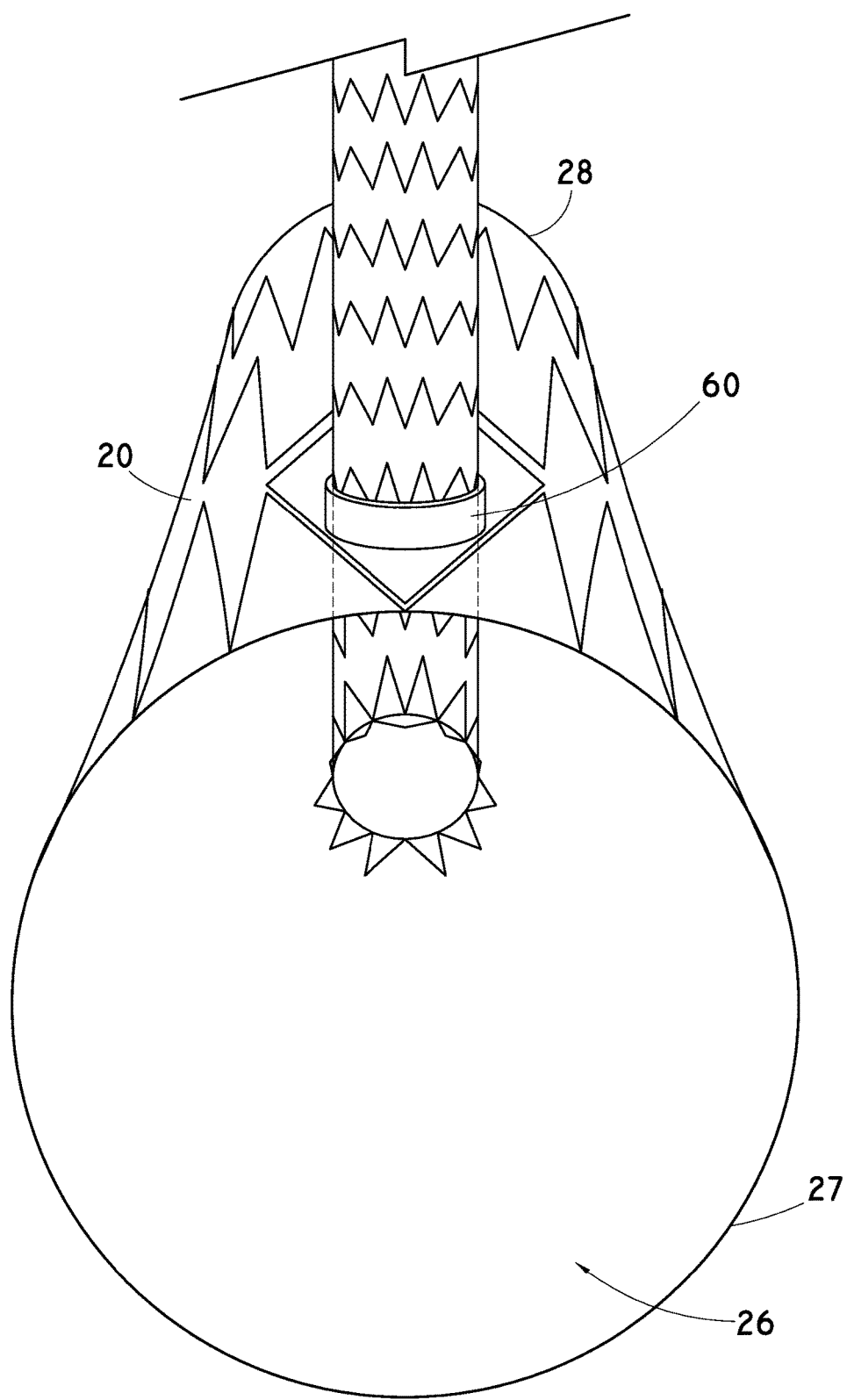
FIG. 18 is a perspective view along a lumen of the endoluminal prosthesis of FIGS. 16-17 with the branch prosthesis deployed therein.

A branch prosthesis, such as a stent graft, may be deployed within the branch 60 as shown in FIGS. 16-18. The branch prosthesis may be delivered over the catheter 82 and deployed within the branch 60 using any known method. The branch prosthesis may extend proximally from the branch 60 as shown in FIG. 16, distally from the branch as shown in FIG. 17, or any other direction according to the position of the branch relative to the graft body 20. The branch prosthesis may extend between a position within the lumen 26 of the graft body 20 and a position external to the graft body as shown in FIG. 18. A lumen of the branch prosthesis may be in communication with the lumen 26 of the graft body 20. In one example, the branch prosthesis may extend between the lumen 26 of the graft body 20 and a branch vessel such as the left subclavian artery. In other words, a first end of the branch prosthesis may be deployed within the branch 60 of the prosthesis 10 and a second end of the branch prosthesis may be deployed within the left subclavian artery. In this manner, the branch prosthesis may couple the prosthesis 10 to the left subclavian artery to create a continuous fluid passageway therebetween.

Figure 19:
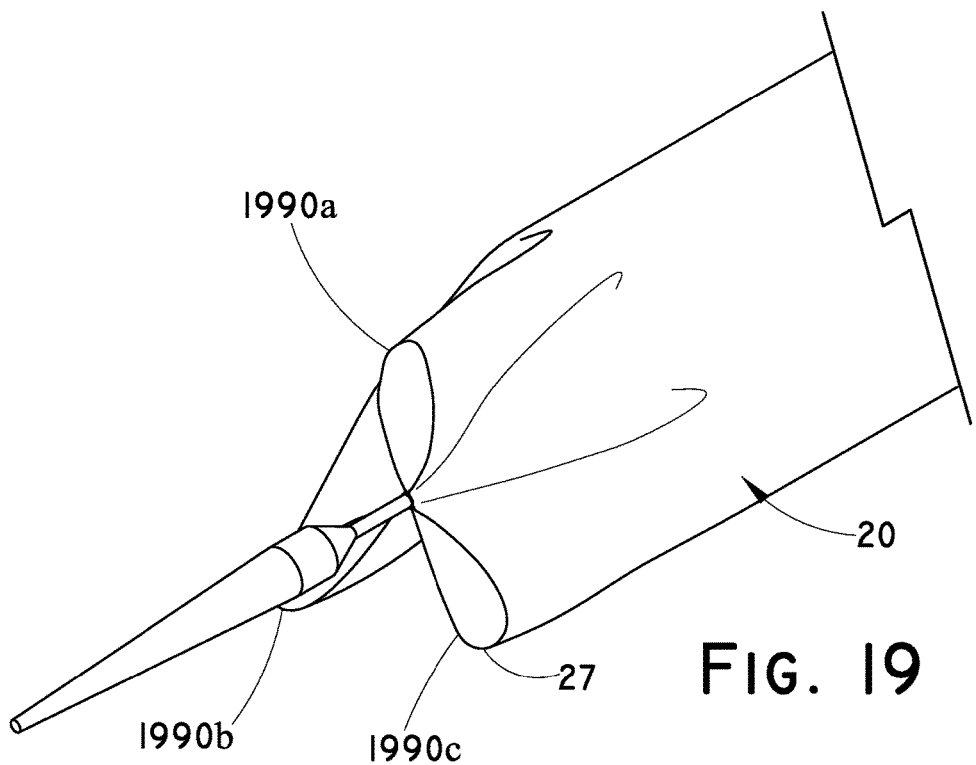
FIGS. 19-20 illustrate different embodiments of retention arrangements for constraining a proximal end of a prosthesis.

The introducer may include a retention arrangement to hold at least a portion of the prosthesis 10 on the introducer. For example, the proximal end 27 of the graft body 20 may be constrained by a retention arrangement as shown in FIG. 19. The retention arrangement may be similar to the arrangement described in U.S. Patent Application Pub. No. 2006/0004433 by Greenberg et al., which is incorporated herein by reference. Three points around the periphery of the graft body 20 may be releasably attached to the introducer. These three points may correspond to three peaks of a proximal stent (such as the first proximal stent 30*a* and/or the third proximal stent 630, 830, and/or 1030). This retention arrangement may form three lobes 1990*a*, 1990*b*, 1990*c* of graft material arranged around the introducer in a tri-fold configuration.

Figure 20:
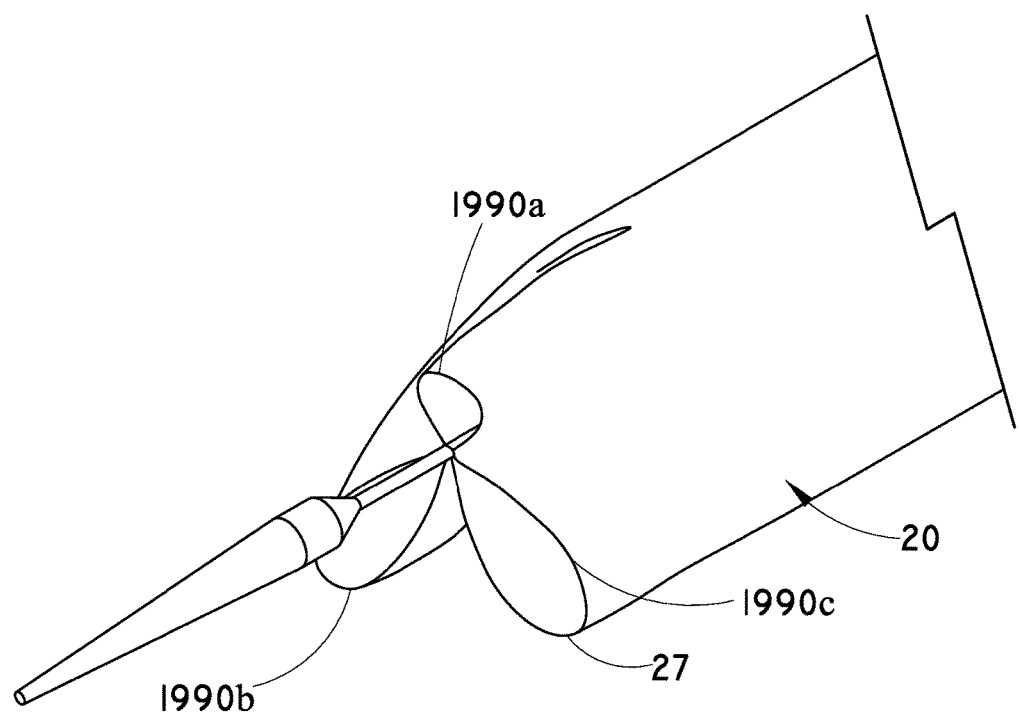

In another example, the proximal end 27 of the graft body 20 may be constrained by a retention arrangement as shown in FIG. 20. This arrangement may be substantially similar to the arrangement shown in FIG. 19 except that multiple peaks of the proximal stent corresponding to at least one of the lobes may be releasably attached to the introducer to form a modified tri-fold configuration such as the configuration shown in FIG. 20. For example, a circumferential portion of the proximal stent may correspond to the lobe 1990*a*. Each of the peaks of that circumferential portion of the proximal stent may be releasably attached to the introducer to reduce the size of the lobe 1990*a* relative to the other lobes 1990*b*, 1990*c*. The lobe 1990*a* may be generally circumferentially aligned with the branch 60 and may be configured for placement along the outer curvature of the aortic arch. In other words, the lobe 1990*a* having a reduced size relative to the other lobes 1990*b*, 1990*c* may be positioned along the greater curvature of the aortic arch. The reduced size of the lobe 1990*a* may reduce the likelihood of the lobe 1990*a* catching or snagging on a branch vessel such as the left subclavian artery upon deployment, positioning, and/or repositioning of the prosthesis 10 within the aortic arch.

The introducer may be configured to enhance conformance of the prosthesis to the curvature of the aortic arch. In one example, the delivery catheter may include a curved inner cannula 2192 as shown in FIG. 21. The curved inner cannula 2192 may be formed from a shape memory material and may have a radius of curvature ranging from about 0.5 cm to about 3.5 cm. A smaller radius of curvature may provide a greater urging force which may be advantageous for use in tight vascular bends. The prosthesis 10 may be compressed into the delivery configuration and mounted to the curved cannula 2192 as described above. The curved cannula 2192 may be held substantially straight within the sheath of the introducer. Upon retraction of the sheath, the curved cannula 2192 may flex toward the natural curved configuration to generally conform to the curvature of the aortic arch. The curved cannula 2192 may push the prosthesis 10 toward the outer curvature of the aortic arch as shown in FIG. 21. Alternatively, the curved cannula 2192 may be configured to pull the prosthesis 10 toward the inner curvature of the aortic arch. This may aid in conforming the prosthesis 10 to the curvature of the aortic arch and/or aligning the branch 60 with a branch vessel such as the left subclavian artery. The branch 60 may be generally circumferentially aligned with the greater curvature or the outer curvature of the curved cannula 2192. Thus, when the curved cannula 2192 is aligned with the curvature of the aortic arch, the branch 40 may be automatically aligned circumferentially with the branch vessels of the aortic arch. Alternatively, or additionally, the introducer may include a curved sheath. The curved sheath may generally conform to the curvature of the aortic arch in a similar manner and with similar results. In other words, a curved cannula or sheath may automatically orient the prosthesis in line with the curvature of the aorta. In the case of arch vessels, which are generally located on the outer curve of the aorta, any branches can be aligned with the greater curvature of the delivery system. When tracked into position, the system may automatically align the branch with the target arch vessel.

Figure 22:
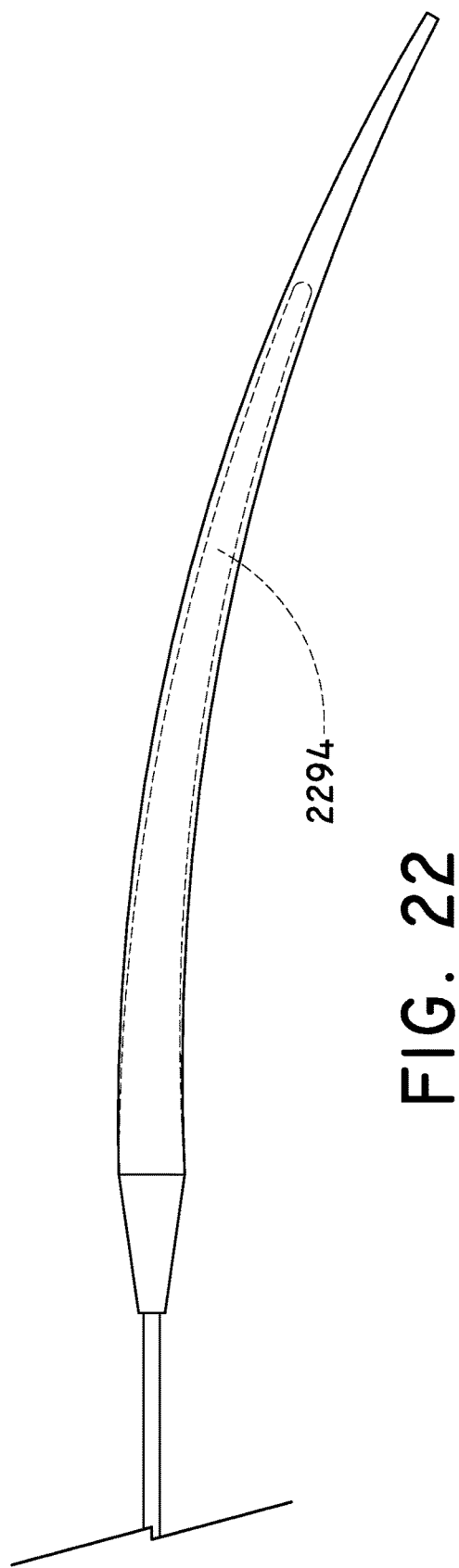
FIG. 22 illustrates one embodiment of an introducer having a curved dilator tip.

In another example, the distal end of the introducer may include a curvature to provide a self-orienting effect to the introducer. For example, the introducer may include a curved dilator tip 2294 as shown in FIG. 22. The prosthesis 10 may be mounted on the introducer such that the branch 60 may be generally circumferentially aligned with the outer curvature of the introducer. Upon placement in the aortic arch, the outer curvature of the introducer may align itself with the outer curvature of the aortic arch. This, in turn, may cause the branch 60 to be generally circumferentially aligned with a branching vessel such as the left subclavian artery. Such alignment may be substantially automatic. In other words, the curvature of the introducer may naturally tend to align with the curvature of the aortic arch without additional manipulation by the physician. This automatic alignment may aid in proper positioning of the prosthesis 10 within the aortic arch. More specifically, rotational adjustment of the delivery device may be challenging or even impossible, especially when a femoral approach is used. Significant tortuosity in the iliac arteries, the visceral segment, the descending thoracic aorta, and the aortic arch may add to the difficulty of such rotational adjustment. A means to automatically orient or align the delivery device and/or the prosthesis 10 within the aortic arch may help to avoid the necessity to rotate the delivery device, thus aiding in positioning of the prosthesis.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. An endoluminal prosthesis system comprising:
a main graft body, the main graft body comprising:
   a sidewall,
   a proximal end, and
   a distal end;
a first stent positioned near the proximal end of the main graft body, and a second stent positioned adjacent to and distal of the first stent, each of the first stent and the second stent comprising a series of peaks and a series of valleys;
an opening in the sidewall positioned longitudinally between one of the peaks of the first stent and one of the valleys of the second stent; and
a tubular branch attached to the main graft body, the tubular branch comprising a first end opening and a second end opening, the tubular branch extending from the opening and attached to the main graft body at the opening at a point of attachment about a circumference of the tubular branch, the tubular branch being flexibly orientable between a retrograde configuration and an antegrade configuration, wherein, in the retrograde configuration, the first end opening is oriented toward the distal end of the main graft body and the second end opening is oriented toward the proximal end of the main graft body, and, in the antegrade configuration, the first end opening is oriented toward the proximal end of the main graft body and the second end opening is oriented toward the distal end of the main graft body;
a third stent positioned near the proximal end of the main graft body, the third stent comprises a greater number of peaks and valleys than the first stent, the third stent is positioned proximal of the first stent, and the first stent and the third stent are in a nested relationship with one another; and
wherein the proximal end of the main graft body comprises a slanted end, and a top longitudinal length of the main graft body is longer than a bottom longitudinal length of the main graft body to form the slanted end.

2. The prosthesis system of claim 1, wherein the opening in the sidewall is a slit that extends at least partially circumferentially around the main graft body, the tubular branch comprises a first portion that extends inward from the sidewall, a second portion that extends-outward from the sidewall, and an intermediate portion that is attached to the sidewall at the point of attachment.

3. The prosthesis system of claim 2, wherein the slit comprises a length of between about ⅖ of a circumference of the branch and about ½ of the circumference of the branch.

4. The prosthesis system of claim 1, wherein the sidewall comprises a deformable graft region and an at least partially supported perimeter about the deformable graft region, the deformable graft region disposed between the first stent and the second stent and free of any stenting within the deformable graft region, wherein the opening in the sidewall is positioned within the deformable graft region, and the tubular branch extends outward from the deformable graft region.

5. The prosthesis system of claim 1, wherein the tubular branch further comprises a biocompatible graft material and a support structure attached to the biocompatible graft material of the tubular branch, and the support structure of the tubular branch comprises at least one of a Z-stent, a helical stent, or an annular ring.

6. The prosthesis system of claim 1, wherein the tubular branch is spaced from the proximal end of the tubular main graft body by a distance of between about 5 mm and about 30 mm.

7. The prosthesis system of claim 1, wherein the tubular branch is positioned longitudinally at least partially between one of the peaks of the first stent and one of the valleys of the second stent and circumferentially between adjacent struts of the first stent.

8. The prosthesis system of claim 1, wherein the first stent is attached to an inner surface of the main graft body, one of the series of peaks comprises a widened peak comprising a greater angle than an adjacent peak, and the widened peak is circumferentially aligned with the tubular branch.

9. The prosthesis system of claim 1, wherein the first stent is attached to an inner surface of the main graft body, the third stent is attached to an outer surface of the main graft body, a first peak of the third stent is circumferentially aligned with each of the tubular branch and one of the peaks of the first stent, and a second peak of the third stent is circumferentially aligned with one of the valleys of the first stent.

10. The prosthesis system of claim 1, wherein the first stent is attached to an inner surface of the main graft body, one of the series of peaks comprises a widened peak comprising a greater angle than an adjacent peak, and the widened peak is circumferentially aligned with the tubular branch;
   wherein the slit is positioned longitudinally between the widened peak and one of the valleys of the first stent, extending at least partially circumferentially around the main graft body between adjacent struts of the first stent, and comprising a length of between about ⅖ of a circumference of the branch and about ½ of the circumference of the branch;
   wherein the tubular branch comprises a first portion extending inward from the sidewall, a second portion extending outward from the sidewall, an intermediate portion attached to the sidewall at the point of attachment, a biocompatible graft material, and a support structure attached to the biocompatible graft material of the tubular branch and comprising at least one of a Z-stent, a helical stent, or an annular ring.

11. The prosthesis system of claim 1, further comprising a catheter extending within each of the main graft body and the tubular branch in a preloaded configuration, wherein the catheter extends through a distal end opening of the main graft body and within the tubular branch for retrograde delivery of the prosthesis.

12. The prosthesis system of claim 1, further comprising a catheter extending within each of the main graft body and the tubular branch in a preloaded configuration, wherein the catheter extends through a proximal end opening of the main graft body and within the tubular branch for antegrade delivery of the prosthesis.

13. An endoluminal prosthesis system comprising:
   a tubular main graft body, the tubular main graft body comprising:
      a sidewall,
      a proximal end, and
      a distal end;
   a first stent positioned near the proximal end of the main graft body, and a second stent positioned adjacent to and distal of the first stent, each of the first stent and the second stent comprising a series of peaks and a series of valleys;
   an opening in the sidewall positioned longitudinally between one of the peaks of the first stent and one of the valleys of the second stent;
   a tubular branch comprising a first end opening and a second end opening, the tubular branch extending from the opening in the sidewall and attached to the main graft body at the opening in the sidewall at a point of attachment about a circumference of the tubular branch and intermediate the first end opening and the second end opening, the tubular branch being flexibly orientable between a retrograde configuration and an antegrade configuration, wherein, in the retrograde configuration, the first end opening is oriented toward the distal end of the main graft body and the second end opening is oriented toward the proximal end of the main graft body, and, in the antegrade configuration, the first end opening is oriented toward the proximal end of the main graft body and the second end opening is oriented toward the distal end of the main graft body;
   a third stent positioned near the proximal end of the main graft body, the third stent comprises a series of peaks and a series of valleys, the third stent comprises a shorter amplitude than the first stent and a greater number of peaks and valleys than the first stent, the third stent is positioned proximal of the first stent, and the first stent and the third stent are in a nested relationship with one another.

14. An endoluminal prosthesis system comprising:
   a tubular main graft body, the tubular main graft body comprising:
      a sidewall,
      a proximal end, and
      a distal end;
   a first stent positioned near the proximal end of the main graft body, and a second stent positioned adjacent to and distal of the first stent, each of the first stent and the second stent comprising a peak and a valley;
   an opening in the sidewall positioned longitudinally between the peak of the first stent and the valley of the second stent;
   a tubular branch comprising a first end opening and a second end opening, the tubular branch extending from the opening and attached to the main graft body at the opening at a point of attachment about a circumference of the tubular branch, the tubular branch being flexibly orientable between a retrograde configuration and an antegrade configuration, wherein, in the retrograde configuration, the first end opening is oriented toward the distal end of the main graft body and the second end opening is oriented toward the proximal end of the main graft body, and, in the antegrade configuration, the first end opening is oriented toward the proximal end of the main graft body and the second end opening is oriented toward the distal end of the main graft body; and
   wherein the proximal end of the main graft body comprises a slanted end, and a top longitudinal length of the main graft body is longer than a bottom longitudinal length of the main graft body to form the slanted end.

* * * * *